(12) United States Patent
Burt

(10) Patent No.: US 9,757,422 B2
(45) Date of Patent: Sep. 12, 2017

(54) METHODS AND COMPOSITIONS FOR REGENERATING AND REPAIRING DAMAGED OR AGED TISSUE OR ORGANS USING NONVIABLE IRRADIATED OR LYOPHILIZED PLURIPOTENT STEM CELLS

(71) Applicant: Richard K. Burt, Chicago, IL (US)

(72) Inventor: Richard K. Burt, Chicago, IL (US)

(*) Notice: Subject to any disclaimer, the term of this patent is extended or adjusted under 35 U.S.C. 154(b) by 0 days.

(21) Appl. No.: 15/200,303

(22) Filed: Jul. 1, 2016

(65) Prior Publication Data

US 2016/0310544 A1    Oct. 27, 2016

Related U.S. Application Data

(60) Continuation of application No. 14/280,278, filed on May 16, 2014, now Pat. No. 9,381,151, which is a division of application No. 13/800,281, filed on Mar. 13, 2013, now Pat. No. 9,364,425.

(60) Provisional application No. 61/612,716, filed on Mar. 19, 2012.

(51) Int. Cl.

| | |
|---|---|
| A01N 63/00 | (2006.01) |
| A01N 65/00 | (2009.01) |
| C12N 5/07 | (2010.01) |
| A61K 35/545 | (2015.01) |
| A61K 35/12 | (2015.01) |
| A61K 8/98 | (2006.01) |
| A61Q 19/08 | (2006.01) |
| C12N 5/0735 | (2010.01) |

(52) U.S. Cl.
CPC ............ *A61K 35/545* (2013.01); *A61K 8/981* (2013.01); *A61K 8/982* (2013.01); *A61K 35/12* (2013.01); *A61Q 19/08* (2013.01); *C12N 5/0606* (2013.01)

(58) Field of Classification Search
None
See application file for complete search history.

(56) References Cited

U.S. PATENT DOCUMENTS

| | | | |
|---|---|---|---|
| 5,486,359 | A | 1/1996 | Caplan |
| 5,827,735 | A | 10/1998 | Young |
| 5,837,539 | A | 11/1998 | Caplan |
| 7,311,905 | B2 | 12/2007 | Hariri |
| 8,187,881 | B2 | 5/2012 | Smith |
| 9,017,658 | B2 | 4/2015 | Burt |
| 2002/0188963 | A1 | 12/2002 | Loring |
| 2004/0151704 | A1 | 8/2004 | Berenson |
| 2005/0106724 | A1 | 5/2005 | Schierholz |
| 2005/0255588 | A1 | 11/2005 | Young |
| 2007/0092494 | A1 | 4/2007 | Higgins |
| 2007/0274960 | A1 | 11/2007 | Harman |
| 2007/0292401 | A1* | 12/2007 | Harmon ........... A61K 35/28 424/93.21 |
| 2008/0241113 | A1 | 10/2008 | Walton |
| 2009/0214491 | A1 | 8/2009 | Burt |
| 2010/0209398 | A1 | 8/2010 | Tankovich |
| 2011/0020291 | A1 | 1/2011 | Banerjee |
| 2011/0212062 | A1 | 9/2011 | Falanga |
| 2012/0141433 | A1 | 6/2012 | Tankovich |
| 2013/0243739 | A1 | 9/2013 | Burt |
| 2014/0255357 | A1 | 9/2014 | Burt |
| 2015/0328265 | A1 | 11/2015 | Burt |
| 2016/0022744 | A1 | 1/2016 | Burt |

FOREIGN PATENT DOCUMENTS

| | | |
|---|---|---|
| CN | 101449822 | 6/2009 |
| WO | 2004007697 | 1/2004 |
| WO | 2008011524 | 1/2008 |

OTHER PUBLICATIONS

Brown, Kristy J., et al., "Advances in the Proteomic Investigation of the Cell Secretome." Expert Rev Proteomics, Jun. 2012, vol. 9, No. 3, pp. 337-345.
Choi, Dong-Sic, et al., "Proteomics of Extracellular Vesicles: Exosomes and Ectosomes." Mass Spectrometry Reviews, 2015, vol. 34 pp. 474-490.
Chute, John P., et al., "Ex vivo culture rescues hematopoietic stem cells with long-term repopulating capacity following harvest from lethally irradiated mice." Experimental Hematology, vol. 32, 2004, pp. 308-317.
Colombian Patent Application No. 09-015685, Colombian Office Action, 2 pages.
Dai, Wangde, et al., "Myocardial Regeneration by Embryonic Stem Cell Transplantation: Present and Future Trends." Expert Review of Cardiovascular Therapy, vol. 4, No. 3, May 2006, pp. 375-383.
European Patent Application No. 07840442.3, Examination Communication, dated Aug. 29, 2011, 4 pages.
European Patent Application No. 07840442.3, Extended European Search Report, dated Mar. 24, 2010, 5 pages.
Fraidenraich, Diego, et al., "Rescue of Cardiac Defects in Id Knockout Embryos by Injection of Embryonic Stem Cells." Science, Oct. 8, 2004, vol. 306, pp. 247-252.
Hassink, Rutger J., et al., "Stem Cell Therapy for Ischemic Heart Disease." Trends in Molecular Medicine, Oct. 2003, vol. 9, pp. 436-441.
Heng, B.C., et al., "Utilizing Human Embryonic Stem Cells As 'Catalysts' for Biological Repair and Regeneration: Challenges and Possible Strategies." Clinical and Experimental Medicine, May 2005, vol. 5, No. 1, pp. 37-39.

(Continued)

*Primary Examiner* — Thomas J Visone
(74) *Attorney, Agent, or Firm* — Fitch, Even, Tabin & Flannery LLP

(57) ABSTRACT

Compositions and methods are provided herein for regenerating and repairing damaged or aged tissue or organs using nonviable lethally irradiated or lyophilized pluripotent stem cells. In one aspect, the compositions and methods described herein provide anti-aging benefits to the skin by increasing the hydration reducing fine lines, wrinkles, and pores of the skin. Compositions and methods are also provided for promoting wound healing using lyophilized pluripotent stem cell powder. A method is provided for inducing cardiac muscle regeneration in a primate comprising delivering nonviable lethally irradiated pluripotent stem cells to damaged or aged areas of the heart. The compositions and methods include nonviable lethally irradiated or lyophilized pluripotent stem cells. In one aspect, the compositions and methods utilize nonviable pluripotent stem cells in the form of a powder, such as lyophilized stem cells.

12 Claims, 16 Drawing Sheets

(56) References Cited

OTHER PUBLICATIONS

Heng, Boon Chin, et al., "Potential Benefits of Co-transplanting Autologous Adult Stem Cells Together With Human Embryonic Stem Cells or Their Differentiated Derivatives." Annals of Clincal and Laboratory Science, vol. 35, No. 1, Jan. 2005, pp. 3-6.
Heng, Boon Chin, et al., "Transplanted Human Embryonic Stem Cells as Biological 'Catalysts' for Tissue Repair and Regeneration." Medical Hypotheses, vol. 64, No. 6, 2005 pp. 1085-1088.
Hodgson, Denice M., et al., "Stable Benefit of Embryonic Stem Cell Therapy in Myocardial Infarction." Am. J. Physiol. Heart Circ. Physiol., 2004, 287 (2), H471-H479.
International Application No. PCT/US2007/073904, International Search Report and Written Opinion of the International Search Authority, dated Aug. 29, 2008, 6 pages.
International Application No. PCT/US2013/030850, International Search Report and Written Opinion of the International Search Authority, dated May 21, 2013, 8 pages.
Ke, Qingen, et al., "Embryonic Stem Cells Cultured in Biodegradable Scaffold Repair Infarcted Myocardium in Mice." Acta Physiologica Sinica, 2005, 57 (6), pp. 673-681.
Lee, Jong-Kuen, et al., "Exosomes Derived from Mesenchymal Stem Cells Suppress Angiogenesis by Down-Regulating VEGF Expression in Breast Cancer Cells." PLOS ONE, Dec. 2013, vol. 8, issue 12, pp. 1-11.
Schey, Kevin L., et al., "Proteomics Characterization of Exosome Cargo." Methods, Mar. 2015, <http://doi.org/10.1016/j.ymeth.2015.03.018>, pp. 1-8.
Singapore Patent Application No. 11201405875P, Search Report, Oct. 5, 2015, 5 pages.
Singapore Patent Application No. 11201405875P, Written Opinion, Oct. 16, 2015, 8 pages.
Singapore Patent Application No. 200900053-0, Search and Examination Report, Jun. 18, 2010, 7 pages.
Tauro, Bow J., et al., "Two Distinct Populations of Exosomes Are Released from LIM1863 Colon Carcinoma Cell-Derived Organoids." Molecular & Cellular Proteomics, 12.3, pp. 587-597.
Trounson, Alan. "Human Embryonic Stem Cells: Mother of All Cell and Tissue Types." Reproductive Biomedicine Online, Reproductive Healthcare Ltd, Cambridge, vol. 4, No. 1, Jan. 1, 2002, pp. 58-63.
Watson, G.E., et al., "Long-term in Vivo Transmission of Alpha-particle-induced Chromosomal Instability in Murine Haemopoietic Cells." International Journal of Radiation Biology, vol. 69, No. 2, 1996, pp. 175-182.

* cited by examiner

METHODS AND COMPOSITIONS FOR REGENERATING AND REPAIRING DAMAGED OR AGED TISSUE OR ORGANS USING NONVIABLE IRRADIATED OR LYOPHILIZED PLURIPOTENT STEM CELLS

CROSS REFERENCE TO RELATED APPLICATIONS

This application is continuation of U.S. application Ser. No. 14/280,278, filed May 16, 2014, which is a divisional application of U.S. application Ser. No. 13/800,281, filed Mar. 13, 2013, now U.S. Pat. No. 9,364,425, which claims the benefit of U.S. Provisional Application No. 61/612,716, filed Mar. 19, 2012, which are incorporated herein by reference in their entireties.

FIELD

This disclosure relates to the repair and treatment of aged or damaged organs and tissues.

BACKGROUND

Cells derived from pluripotent stem cells, also referred to herein as embryonic stem cells ("ESC"), are being investigated as agents to repair or rejuvenate tissue. However when injected in vivo, ESC, due to their pluripotential, form teratomas, i.e. dysregulated, cancerous tumor growths.

To avoid generation of teratomas or disorderly growth in vivo, the ESC presently being developed for transplantation are differentiated ex vivo into lineage committed adult stem cell phenotypes and/or fully differentiated cells. This process is time consuming and generally requires maintenance of Good Manufacturing Procedures (GMP) over an extended period of time. The differentiated cells must be purified to ensure that there is no contamination from residual pluripotent ESC. The process must also include a method to ensure desired cell identity and lot-to-lot equivalency.

Transplanted ESC-derived cells produced by current methods require lifetime immune suppression to prevent immune mediated rejection of ESC-derived cells. Many immunosuppressants are also cytotoxic and include antimetabolites (azathioprine), alkylating agents (cyclophosphamide), and folic-acid antagonists (methotrexate or 6-MP). Other immunosuppressants include mycophenolate mofetil (CellCept® from Hoffmann-La Roche, Inc.) and cyclosporin. These drugs may cause numerous side effects including lethal infections.

Transplantation of ESC-derived cells requires the use of viable live cells that have a very limited shelf life. Maintaining cell viability requires local on site production for immediate infusion and or cryopreservation (freezing) in agents such as DMSO before overnight shipping on dry ice to prevent thawing. The frozen cells must then be thawed, washed to remove cytotoxic cryo-preservatives like DMSO, sterility rechecked, and viability reconfirmed before infusion, all of which increases expense and limits availability and practical application.

SUMMARY

Methods and compositions are provided herein for regenerating and/or repairing aged, degenerating, injured, diseased, or otherwise damaged organs and tissues in a subject using nonviable pluripotent stem cells that have been either lethally irradiated or lyophilized. In this latter aspect, pluripotent stem cells (e.g., embryonic stem cells or "ESC") are frozen and then vacuum dried to a powder that has an indefinite shelf life at room temperature and may be applied locally or dissolved into a solution before injection in an amount effective to provide a desired therapeutic effect. Lyophilized ESC may be manufactured at one site, do not require cryopreservation, have an indefinite shelf life, do not require immune suppression, and may be distributed globally to hospitals, pharmacies, or other locations to be reconstituted and injected on location similar to lyophilized proteins, antibodies, and drugs.

As described herein, in one aspect, an anti-aging benefit is provided to the skin by topical application of lyophilized human ESC to increase the hydration of human skin and reduce fine lines, wrinkles, pores, and skin roughness. In another aspect, a method is provided for promoting wound healing using either lethally irradiated ESC or lyophilized ESC powder. In yet another aspect, a method is provided for intracardiac, intracoronary, and/or intravenous injection into the heart to induce cardiac muscle regeneration. Nonviable lethally irradiated ESC and lyophilized ESC, vesicles, or fragments thereof are immune independent, do not require tissue typing, and may be utilized to repair any tissue or organ.

Neither the lethally irradiated ESC nor lyophilized pluripotent stem cell powder described in the compositions and methods herein are able to grow or divide in vivo or in vitro. The lyophilized stem cells are in the form of a powder of nonviable cells and or cellular contents that cannot be reconstituted into viable cells. The powdered form does not include living cells following the lyophilization or freeze vacuum desiccation process. Advantageously, the pluripotent stem cells killed with either lethal doses of irradiation or converted into a powder by lyophilization retain capability to repair damaged or degenerating organs or tissues in a subject.

A composition and method is provided for an anti-aging benefit to human skin. By one approach, the composition is a topical formulation comprising lyophilized pluripotent stem cell powder in an amount effective to provide a desired anti-aging cosmetic benefit to the skin. The method for providing an anti-aging benefit comprises administering an anti-aging or cosmetic composition comprising lyophilized pluripotent stem cells in a cosmetically acceptable carrier to the skin of the subject. For example, treatment with the lyophilized pluripotent stem cell powder is effective to provide the skin with a more youthful appearance due to increased hydration of the skin and a reduction in pores, skin roughness, and fine lines and/or wrinkles.

In yet another aspect, a composition is provided comprising lyophilized pluripotent stem cell powder which can be applied to a wound to promote wound healing. A method is also provided for promoting wound healing comprising administering a therapeutically effective amount of lyophilized pluripotent stem cell powder to a wound of a subject. Promoting wound healing comprises, for example, accelerating wound closure.

In another aspect, pluripotent stem cell powder can be used to regenerate or repair cardiac muscle that has been damaged through, for example, age, disease, ischemia, or degeneration. In this respect, a method is provided for regenerating cardiac muscle comprising applying lyophilized pluripotent stem cell powder reconstituted in saline and injected into a damaged or aged area or vessel of the heart.

DETAILED DESCRIPTION

Figure 1:
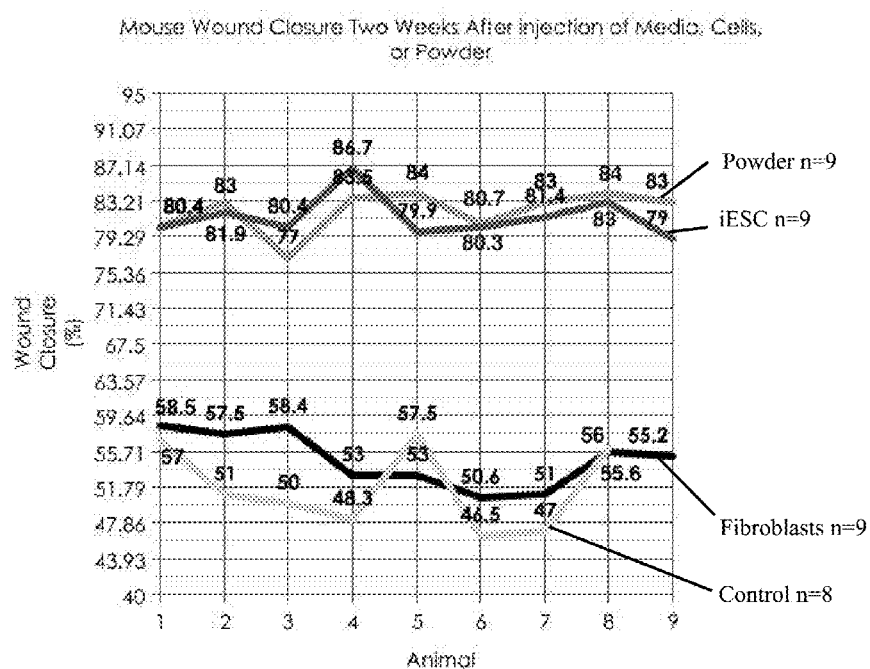
FIG. 1 is a graph demonstrating that pluripotent (embryonic) stem cell powder as well as lethally irradiated embryonic stem cells increase the rate at which murine wounds close compared to fibroblast and media only controls.

The methods and compositions provided herein are based on the discovery, as described in more detail herein, that nonviable lethally irradiated or lyophilized pluripotent stem cells can be used to repair aged, degenerating, injured, diseased, or otherwise damaged organs and tissues (such as skin, wounds, heart, brain, spinal cord, lung, liver, and kidneys) in a subject, including primate subjects, and more particularly in human subjects. At least for some applications, it is preferred that the nonviable pluripotent stem cells are in powder form (e.g., lyophilized). It was surprisingly discovered that nonviable pluripotent stem cells or lyophilized pluripotent stem cells (which may include nonviable intact cells or fragments thereof) have therapeutic benefit. For instance, it was unexpectedly found that lyophilized pluripotent stem cells that are dead and desiccated were shown to have similar effectiveness to lethally irradiated pluripotent stem cells that are able to live for hours or at most days in the body after administration to a subject.

The lyophilized powdered stem cells advantageously can be stored, such as in sealed vials or ampules, for long periods of time and used on an as needed basis. Due to their indefinite shelf stability, the powdered stem cells provide great flexibility to the applications in which the lyophilized pluripotent stem cell powder can be used. The lyophilized pluripotent stem cells in powdered form are not viable upon hydration, reconstitution, or suspension in liquid or other media before administration to a subject. The powdered cells can also be administered to a subject in powder form without reconstitution.

In one aspect, a method and composition are described for providing an anti-aging benefit to the skin. The method comprises delivering lyophilized pluripotent stem cell powder to the skin. The anti-aging benefit includes, for example, increased skin hydration and reduction in pores, wrinkles, fine lines, and skin roughness. The anti-aging benefits resulting from treatment with the lyophilized pluripotent stem cell powder provide the skin with a more youthful appearance.

In another aspect, a composition and method is provided for promoting wound healing in a subject. The wound healing composition comprises either lethally irradiated pluripotent stem cells or lyophilized powder of pluripotent stem cells and the method comprises administering the wound healing composition to a wound of a subject. The wound may be any type of wound, including acute or chronic internal or external injuries, for example, an abrasion, cut, puncture, incision, laceration, ulcer, burn, and the like. In one approach, the wound healing composition comprises nonviable pluripotent stem cells in powder form. It was surprisingly found that nonviable pluripotent stem cells, particularly those in powder form, are effective to accelerate closure of wounds.

Applicant's copending application, U.S. Pub. No. 2009-0214491, which is incorporated herein by reference in its entirety, includes data showing that mitotically inactivated pluripotent stem cells have been used to improve cardiac relaxation and contractility in ischemic murine myocardium. The instant application includes data showing that the methods described herein are effective to repair organs and tissues in primates using human nonviable ESC. In one aspect, a method is provided for inducing cardiac muscle regeneration in a primate (including humans) comprising delivering nonviable pluripotent stem cells to a damaged or aged area or vessel of the heart. The methods herein have now also been shown to be effective to repair organs and tissues using lyophilized pluripotent stem cell powder.

Advantageously, unlike many other stem cell therapies, the beneficial effects provided by nonviable pluripotent stem cells are not dependent on a permanent presence of the delivered stem cells in the target tissue or organ. It is presently believed that the nonviable stem cells are cleared from the body within a short period of time. The lyophilized ESC powder comprises the dried "skeletal" ESC contents including the proteins and lipids of the pluripotent stem cells and, as such, does not include viable intact cells. Accordingly, the immune system of the subject being treated with the lethally irradiated or lyophilized stem cells does not need to be suppressed during or after treatment with the stem cells. Reducing or obviating the need for life long immunosuppression therapy can greatly improve a subject's comfort and quality of life. Advantageously, the nonviable cells do not form teratomas in vivo.

By "nonviable" is meant that the stem cells are prohibited from growing or dividing and in fact are already dead (e.g. lyophilized) or in the process of dying or undergoing apoptosis within a few days to weeks (e.g. lethally irradiated). As used herein, nonviable cells may be produced by any method that causes cell death, such as lethal radiation induced apoptosis or death from freeze drying (e.g., lyophilization). In instances where the stem cells are made nonviable by lyophilization or similar technique, the lyophilization process kills the cells and the cells are not viable for any period of time after administration to the subject. The integrity of the nonviable stem cells may or may not be maintained, but the cellular contents should be preserved with minimal degradation such that function and activity of the contents is substantially maintained.

In the methods described herein, the nonviable pluripotent stem cells are delivered in an effective amount to a damaged or aged tissue or organ in a subject in need of treatment. As used herein, the term "subject" includes mammals, such as but not limited to rodents, pigs, cats, dogs, and primates, and specifically includes humans. The term "effective amount" or "therapeutically effective amount" means the amount that will elicit the biological or medical response of a subject that is being sought by a medical doctor or other clinician. In one aspect, the term "effective amount" is intended to mean the amount that will bring about a biologically meaningful improvement in the treated tissue or organ. Data obtained from animal studies can be used in formulating a range of dosages for human use. The dosage may vary depending upon the dosage form employed, sensitivity of the patient, and the route of administration. The dosage suitable for a given subject can be determined by one of skill in the art. Generally, dosage and administration can be adjusted to provide or to maintain the desired effect. By this approach, the method includes delivering an effective amount to the damaged tissue or organ of a subject in need of regeneration.

Stem Cells

Pluripotent stem cells have the potential to differentiate into endoderm, mesoderm, and ectoderm. As used herein, "pluripotent" includes pluripotent stem cells from all sources, including embryonic stem cells (ESCs), modified adult stem or somatic cells (ASCs), that is, induced pluripotent stem cells (iPSC), and very small embryonic-like stem cells (VSELs).

Pluripotent stem cells traditionally arise from the blastocyst stage of embryonic development and have the ability to develop into all types of fetal and adult cells except perhaps for placenta. Embryonic pluripotent stem cells (ESC) generally can be isolated from a 50- to 150-cell, 4- to 5-day-old post-fertilization blastocyst. While ESCs are capable of indefinite ex vivo proliferation, they exist only transiently in vivo during embryogenesis. Pluripotent stem cells have also been artificially generated (i.e., induced pluripotent stem cells (iPSC)) from other sources, such as placenta or from genetic manipulation of adult stem cells (ASC) or even adult somatic cells. ASC are located in tissues throughout the body and function as a reservoir to replace damaged or aging cells. ASC are generally restricted in their differentiation to cell lineages of the organ system from which they originate (i.e., "multipotent" stem cells), although recent research suggests that adult tissues, such as bone marrow, may harbor dormant pluripotent stem cells referred to as "very small embryonic-like stem cells" or "VSELs."

Various animal ESC lines, such as, for example, NIH approved cell line WAO9 human ESCs can be obtained commercially from WiCell Research Institute, Madison, Wis. Human ESC line Cecol-14, utilized herein, can be obtained commercially from Cecolfes, Bogota, Colombia. Of course, other embryonic stem cell lines may be used, if desired.

Adult stem cells can be isolated from mammalian tissue, including from any adult organ, umbilical cord blood, or placenta. The adult stem cells are multipotent, but they may be manipulated to provide pluripotent stem cells (iPSC) using conventional techniques.

ESC have great versatility but, compared to ASC, can be problematic for in vivo treatments due to the tendency of ESC to form teratoma. In contrast, ASC normally do not form teratoma and follow traditional lineage-specific differentiation patterns, fulfilling their physiologic homologous function of replacing normal turnover, aging or damaged tissues.

In one aspect, the stem cells can be derived from mammals, such as but not limited to rodents, pigs, cats, dogs, and primates, including humans.

Nonviable Pluripotent Stem Cells

The pluripotent stem cells useful herein are nonviable. Advantageously, nonviable stem cells do not form teratomas. Surprisingly, nonviable pluripotent stem cells, including pluripotent stem cells that have been lyophilized into a powder, remain capable of repairing damaged or regenerating organs or tissues in a subject. No adverse effects have been noted after treatment.

Prior to inactivation, the stem cells may be grown under suitable culture conditions. By one approach, the stem cells can be plated with a feeder layer for long-term culture of the stem cells. The feeder cells are treated so that the feeder cells do not divide during culturing. Human cells can be used as a feeder layer. For example, human fibroblasts, such as foreskin fibroblasts, can be used as a feeder layer. In one aspect, the stem cells are grown to about 70 percent confluence. In another aspect, the stem cells are grown on coated plates, such as plates coated with gelatin, laminin, collagen, recombinant human proteins, such as recombinant laminin or collagen, as well as commercially available substrates, such as MATRIGEL™ Basement Membrane Matrix from BD Biosciences, or combinations thereof, without a feeder layer for the final passages before collection for use in the methods described herein.

In one aspect, the stem cells may be made nonviable with irradiation, phototherapy, chemical treatment, and/or lyophilization. The selection of the method of making pluripotent stem cells nonviable is not particularly limited, but it is preferred that the method used is effective to retain the intracellular contents of the stem cells. For example, the nonviable pluripotent stem cells useful herein also include nonviable fragments of pluripotent stem cells including vesicles or liposomal membrane encapsulated lyophilized pluripotent stem cell or fragments of pluripotent stem cells. These nonviable fragments may be used alone or in addition to non-viable but intact (i.e., cellular contents remain within the cell membrane) pluripotent stem cells.

While there are a variety of techniques suitable for producing nonviable pluripotent stem cells, the following exemplary techniques are described in more detail. Other techniques may be used, if desired.

Lyophilization. Nonviable stem cells can be prepared by lyophilization using conventional lyophilization techniques to provide a powdered material that is suitable for prolonged storage at room temperature or colder temperatures. Generally, during lyophilization, water is removed from the cells after the cells are frozen and placed under vacuum so that ice in the product changes directly from solid to vapor without passing through the liquid phase. Other methods of freeze-drying or cyrodesiccation may also be used, if desired.

By one approach, the pluripotent stem cells are prepared as cultured as described above and washed, such as with PBS, before collection and lyophilization. In this respect, the lyophilized cells do not include the media in which the cells were cultured, thereby eliminating the possibility that the therapeutic benefit provided by the lyophilized stem cells can be attributed to conditioned media and any secreted factors, metabolites, proteins, or other components in the media.

An exemplary lyophilization technique that may be used is as follows. The cells are pretreated by dispersing them in a freezing solution and then freezing in liquid nitrogen. In one aspect, trehalose may be used as a lyoprotectant or freezing solution during the freezing step, but other lyoprotectants may also be used, if desired. The cells are then transferred to a lyophilizer that maintains a temperature low enough to keep the cells frozen. Vacuum is applied to lower atmospheric pressure to allow sublimation of water (i.e., transition of water from solid phase to vapor phase without forming an intermittent liquid). A variety of lyophilizers are commercially available, from bench top manifolds to very expensive large-scale production freeze driers. Lyophilization is advantageous in that it provides a storage-ready and stable product of stem cell contents in powder form with no viable residual cells or microbes. By one approach, the lyophilization conditions may be selected to substantially maintain the integrity of the cellular proteins so as to preserve protein structure and function but without any viable cells.

Radiation. In one aspect, the stem cells can be exposed to lethal doses of radiation, e.g., 100 Gy single fraction. The precise radiation dose delivered to the cells and length of dose is not critical so long as the cells are rendered nonviable.

Apoptotic Inducing Agent. In yet another aspect, the stem cells can be treated with an agent that induces apoptosis, such as but not limited to Actinomycin D, Camptothecin, Cycloheximide, Dexamethasone, Doxorubicin, Etoposide, and combinations thereof.

In one aspect, the methods described herein can be practiced within a short period of time after lyophilization or lethal inactivation of the pluripotent stem cells or with stem cells that were previously lyophilized and packaged for storage. In one aspect, the lyophilized pluripotent stem cell powder may be dissolved or dispersed in for example saline into a syringe, an implantation device, or the like, depending upon the intended mode of delivery and use. In certain aspects, the lyophilized pluripotent stem cells may be provided in unit dosage form, such that an amount of the composition is provided in single or multi-dose dose containers. Advantageously, pluripotent stem cell compositions in the form of powders and lyophilisates are particularly suited for shipping and long term storage prior to use.

The lyophilized pluripotent stem cell powder described herein may be administered to a subject by a variety of modes of administration. As such, the formulation as well as the concentration of the composition may vary. In one aspect, the composition includes lyophilized pluripotent stem cell powder. In another aspect, the composition may include lyophilized vesicles or lysosomes from pluripotent stem cells. In one aspect, the compositions may be applied directly or topically to target tissues or organs, or to surrounding fluid or tissue. In one aspect, administration to the desired location may be done by catheter, infusion pump, or stent. Liquid formulations can be prepared, such as, for example, in the form of a solution or suspension in a non-toxic, parenterally-acceptable solvent or diluent. In another aspect, the formulation may be a powder or lyophilisate that is reconstituted in a liquid or other media of choice prior to use. In yet another aspect, the formulation may be in the form of an emulsion or liquid concentrate for dilution prior to administration. Exemplary pharmaceutically-acceptable carriers include saline, phosphate buffered saline, isotonic saline, Ringer's solution, dextrose, sterile water, deionized water, glycerol, ethanol, 5% dextrose in water, and combinations thereof. Additional routes of delivery include topical application for treatment of the skin or wound. For topical application, the media to which the nonviable stem cells are added may include, for example, pharmaceutically acceptable carriers, such as creams, ointments, emulsions, and aqueous solutions.

Anti-Aging Skin Treatment

Aging skin can be characterized by the onset of wrinkles and fine lines. The aging of the skin can be accelerated by environmental factors, including exposure to sunlight, diet, and smoking. In one aspect, the topical formulation comprises an amount of pluripotent stem cells lyophilized powder effective to gradually provide a desired anti-aging or cosmetic benefit to the skin. A method is also provided for providing a desired anti-aging benefit by topical application in the form of a crème, lotion, or soap or other cosmetic preparation. Treatment with lyophilized pluripotent stem cells provides the skin with a more youthful and smooth appearance due to increased hydration and a reduction in fine lines, wrinkles, and pore size.

A variety of types of topical formulations for imparting an anti-aging benefit can be provided. By one approach, the topical formulation can be provided in the form of an emulsion, such as a cream or lotion, a stabilized gel, salve, ointment, dispersion, a shampoo or hair conditioner, a treatment serum, a liposomal delivery system, a topical facial pack or mask, a surfactant-based cleansing system, an aerosolized or sprayed dispersion or emulsion, a skin conditioner, styling aid, or a pigmented product such as makeup in liquid, cream, solid, or anhydrous form. Exemplary cosmetics include, for example, lipstick, lip balm, pressed powder, foundation, concealer, and eye creams or shadow. By another approach, topical formulation can be provided at a spa or cosmetic counter in the form of a moisturizer, sunscreen, anti-acne product, or the like. By yet another approach, the topical formulation can be provided in a prescription or over-the-counter pharmaceutical composition. Other formulations may also be provided, if desired. Appropriate cosmetically acceptable vehicles can be selected to formulate the topical composition in the desired form.

The topical formulation may comprise a variety of optional ingredients. For example, the topical formulation may include ingredients such as but not limited to perfume, perfume solubilizing agents, preservatives, coloring agents, and additional active ingredients, if desired. In one aspect, any additional ingredients included in the composition should not negatively impact the integrity of the contents of the lyophilized or nonviable pluripotent stem cells. In one aspect, the topical composition may also include an additional active ingredient, such as, for example, skin penetrating agents, antioxidants, vitamins, provitamins, sunscreen, and derivatives thereof, including, for example, epigallocatechin gallate (EGCG), tocopheryl and ascorbyl derivatives, Vitamin B3, Vitamin B5, Vitamin C, Vitamin E, Vitamin E acetate, panthenol, retinoid, retinol, retinyl, propionate, retinyl palmitate, retinoic acid, and combinations thereof, as well as other actives commonly used in topical treatments, such as salicylic acid, and alpha-hydroxyacid. The composition may also include an exfoliating agent, sun block, or tanning agent if desired.

The topical formulation comprises lyophilized powder of pluripotent stem cells. The optimal dose of nonviable pluripotent stem cells or pluripotent stem cell lyophilized powder may depend, at least in part, on the severity of the condition, method of delivery, and method of inactivation of the pluripotent stem cells. By one exemplary approach, the topical formulation of lyophilized powder would be from trace amounts to milligram or greater concentrations per ounce. By one exemplary approach, the topical formulation may include but is not limited to about $5\times10^4$ to about $1\times10^8$ nonviable pluripotent stem cells, in another aspect about $5\times10^4$ to about $5\times10^7$ nonviable pluripotent stem cells, which may be provided in the form of nonviable intact cells or lyophilized fragments and cellular contents prepared from, for example, about $5\times10^4$ to about $1\times10^8$ pluripotent stem cells per ounce of the topical formulation.

The treatment regimen for reduction of wrinkles and fine lines can vary depending on the particular needs of the subject. For example, the dose and frequency of administration of the topical formulation may depend in part on the age of the subject, condition of the subject's skin, and desired results after treatment. By way of non-limiting illustration, the topical formulation may be applied at least once daily. By another approach, the topical formulation may be applied at least once weekly or on a less frequent basis. Some subjects may benefit from regular application of the formulation. For example, some subjects may benefit from a treatment regimen where the topical formulation is applied at least once or twice or more daily for about 8 weeks. A shorter or longer treatment regimen may be used, if desired. Further, the topical formulation may be applied all over the face or other portion of the body in need of treatment, or may be targeted to specific areas in need of treatment. In some approaches, it may be advantageous to exfoliate the skin prior to application of the topical composition. By one exemplary approach, the hydration level of the skin can be measured by a corneometer, such as CM 825, CK (Cologne, Germany). At least in some approaches, an effective amount of lyophilized pluripotent stem cells is that amount which achieves statistically significant improvement of skin hydration. At least in some approaches, an effective amount of lyophilized pluripotent stem cells is that amount which achieves statistically significant decrease in pore size, fine lines, wrinkles, or skin roughness.

In another aspect, an anti-aging kit is provided. The anti-aging kit may comprise a topical composition comprising lyophilized powder of pluripotent stem cells in a crème, lotion, or other cosmetic formulation and an exfoliant, such as a chemical or mechanical exfoliant, including, for example, loofah, brush, sponge, facial cloth, and facial creams or washes containing sodium bicarbonate, salicylic acid, or alpha-hydroxy acid. In another aspect, the anti-aging kit may comprise a topical composition, such as a cream or lotion, inactivated pluripotent stem cells in powder form for mixing into the topical composition, and optionally an exfoliant.

Wound Healing Treatment

In another aspect, a composition for the treatment of wounds comprising lyophilized pluripotent stem cell powder is provided. The wound healing composition increases the rate of wound healing. The wound to be healed may be a result of a variety of acute or chronic internal or external injuries, diseases, or ailments, including, for example, abrasions, cuts, punctures, incisions, lacerations, ulcers, burns, surgical, bullet, knife, or improvised explosive device induced wounds, and the like.

The lyophilized pluripotent stem cell powder may be applied directly to the wound, applied to a bandage or dressing that covers the wound, or re-suspended in solution and injected into the wound or its penumbra to promote wound healing. In one approach, the wound healing composition is administered to a wound and then the wound can be covered with a conventional wound dressing, gauze, or bandage, if desired. In another approach, the wound healing composition may be administered to the wound as a component of a bandage, transdermal patch, or bioadhesive. By one exemplary approach, the wound healing composition can be applied to a wound at least once daily until the wound has healed. By another approach, the topical formulation can be applied at least once daily after the wound has healed to limit scarring.

By one exemplary approach, the wound healing composition includes an amount of lyophilized pluripotent stem cells effective to increase the rate of wound healing. In one aspect, the wound healing composition comprises lyophilized pluripotent stem cells dispersed in a pharmaceutically acceptable carrier. For example, the wound healing composition may include but is not limited to about $5\times10^4$ to about $1\times10^8$ nonviable pluripotent stem cells, in another aspect about $5\times10^4$ to about $5\times10^7$ nonviable pluripotent stem cells, which may be provided in the form of nonviable intact cells or lyophilized fragments and cellular contents prepared from, for example, about $5\times10^4$ to about $1\times10^8$ pluripotent stem cells per centimeter of tissue or ounce of the wound healing composition.

A method for promoting wound healing in a subject is also provided. The method includes administering a wound healing composition comprising lyophilized pluripotent stem cells to a wound of a subject in need of wound healing. The method may further comprise preparing the wound healing composition by mixing the lyophilized pluripotent stem cells with a pharmaceutically acceptable carrier prior to administering the wound healing composition to the subject. The wound healing composition is delivered to the wound in a therapeutically effective amount to promote wound healing. The composition for the treatment of wounds may further comprise one or more additional components or agents, such as antibiotics or other antimicrobial compounds or agents and other agents known to improve wound healing.

Also provided herein is a kit comprising lyophilized pluripotent stem cells in powder form. The kit may include, for example, media for reconstituting, hydrating, or otherwise suspending the powdered pluripotent stem cells. The kit may also include instructions for mixing the powdered pluripotent stem cells in the media to form a wound treatment composition and for applying the wound treatment composition to a wound. If desired, the kit may further comprise bandages or other dressings.

Regeneration of Cardiac Muscle

In one aspect, lyophilized or nonviable human pluripotent stem cells can be used to regenerate or repair cardiac muscle that has been damaged through age, disease, or degeneration. The affected area of the heart may include, for example, an area of the heart impacting cardiac function. Short and or long term ischemia can result in myocyte death, tissue infarction, and loss of contractile function. For example, the area to be treated may include ischemic penumbra or area best characterized as hibernating myocardium. Hibernating myocardium is a condition due to acute or chronic ischemia where certain portions of the myocardium exhibit abnormal or no contractile function but the cells remain viable.

In another aspect, lethally irradiated pluripotent stem cells or lyophilized pluripotent stem cell powder can be used, for example, in cardiac muscle regeneration for a number of principal indications: (i) acute heart attacks; (ii) therapy for congestive heart failure patients; (iii) prevention of further disease for patients undergoing coronary artery bypass graft; (iv) conductive tissue regeneration; (v) vessel smooth muscle regeneration; (vi) valve regeneration; and (vii) to wean patients from left ventricular assist devices implanted as a bridge to transplant and or destination therapy.

Cardiac muscle normally does not have or has only limited reparative potential. In accordance with the compositions and methods described herein, lethally irradiated pluripotent stem cells and lyophilized pluripotent stem cell powder reconstituted in an agent such as saline are independently able to regenerate cardiac muscle in a subject. In this respect, a method is provided for regenerating or repairing cardiac muscle comprising applying an effective amount of inactivated pluripotent stem cells to a damaged or aged area of the heart. In one aspect, the effective amount for cardiac muscle regeneration or repair is the amount necessary to provide or improve ejection fraction (EF), which is the ratio of stroke volume (SV) to end-diastolic volume (EDV), whereby EF=SV/EDV or decrease infarct size. In this respect, an effective amount of lethally irradiated or lyophilized pluripotent stem cell powder may be the amount necessary to improve ejection fraction or decrease infarct size measured by MRI or other conventional techniques after treatment. Generally, such improvement in ejection fraction and/or decrease in infarct size also serve to improve the quality of life of the subject.

At least in some approaches, an effective amount of lyophilized or nonviable pluripotent stem cells for cardiac muscle regeneration or repair is the amount necessary to improve cardiac ejection fraction by statistically significant amount.

At in some approaches the amount of lyophilized or nonviable pluripotent stem cells for cardiac regeneration is the amount necessary to statistically significantly decrease infarct size.

In one aspect, repeat injection of either lethally irradiated pluripotent stem cells or lyophilized pluripotent stem cell powder reconstituted in a liquid, e.g., saline, are given at standard intervals until therapeutic effect is optimized. The optimal dose may depend, at least in part, on the condition of the organ or tissue and method of delivery. By one approach, about $5\times10^4$ to about $1\times10^8$ nonviable pluripotent stem cells, in another aspect about $5\times10^4$ to about $5\times10^7$ nonviable pluripotent stem cells, which may be provided in the form of nonviable intact cells or lyophilized fragments and cellular contents prepared from, for example, about $5\times10^4$ to about $1\times10^8$ pluripotent stem cells, are delivered to the area of treatment in the subject. Other doses may also be used as needed to provide the desired therapeutic effect.

Depending on the type and extent of injury, it may be advisable to treat the damaged area as soon as possible after injury.

By one approach, treatment of the heart as described herein may provide significant improvement in cardiac function such that no further treatment is necessary. By another approach, treatment of the heart may prolong survival of the subject prior to more radical therapy, including heart transplant.

Chaperone Effect of Pluripotent Stem Cells

Although not wishing to be limited by theory, nonviable pluripotent stem cells, vesicles or lipid encapsulated cellular compartments derived therefrom, or their lyophilized remnants may provide a chaperone (cell-help-cell) effect. Even though nonviable, exchange of information such as intracellular or lipid based proteins, lipids, enzymes, ribonucleic acid, or new signaling pathways with recipient cells may occur. The chaperone effect appears to be required only transiently and appears to be provided by either lethally irradiated or lyophilized pluripotent stem cells before being cleared from or degraded by the body. The chaperone effect does not depend on immune acceptance of the stem cells or on the establishment of a committed or differentiated cell progeny derived directly from the stem cells which advantageously avoids the need for differentiation of stem cells, which generally involves gene therapy or cytokine/media directed ex vivo differentiation, and extensive purification of the stem cell derived somatic cells. The lethally irradiated or lyophilized pluripotent stem cells can be used directly to augment organ or tissue specific regeneration without unwanted side effects of teratoma formation or persistence of a foreign cell. Lyophilized pluripotent stem cell powder or lethally irradiated pluripotent stem cells may thus be viewed as a universal vehicle to repair any human or animal tissues without regard to MHC immune restrictions or need for immune suppression.

In another aspect, nonviable or lyophilized pluripotent stem cells can provide this cell-help-cell effect ex vivo to promote proliferation and recovery of other cell types when grown in culture in a laboratory or commercial facility. In this aspect, a method is provided for promoting the ex vivo growth and expansion of human or animal cell lines, the method including applying nonviable pluripotent stem cells as an ex vivo feeder layer to human cells grown in culture or administrating lyophilized pluripotent stem cell powder at various concentrations to the media. The cells may be any type of human cells, including for example endothelial cells, epithelial cells, fibroblasts, smooth muscle cells, surface epithelial cells, microvascular endothelial cells, myocytes, keratinocytes, melanocytes, and the like derived from any tissue or organ. In one aspect, the nonviable pluripotent stem cells or lyophilized powder are effective to promote the proliferation and/or recovery of the human cell line when grown in culture. The human cell line can then be delivered to a target tissue or organ in a subject in need of treatment. The target for treatment may be a diseased or damaged tissue or organ, such as, for example, the brain, kidney, spinal cord, lung, liver, or heart.

In one aspect, nonviable or lyophilized pluripotent stem cells may function as an in vivo biological matrix or scaffold to promote endogenous repair in vivo in any tissue or organ system.

In another aspect, nonviable or lyophilized pluripotent stem cells can be added to an artificial or ex vivo generated matrix or scaffold to improve organ or tissue regeneration prior to transplantation of the tissue or organ.

The following examples are provided to illustrate certain aspects of the disclosure but should not be construed as limiting the scope of the disclosure. All publications and patents referenced herein are incorporated herein by reference in their entirety. Herein, it is demonstrated that nonviable lethally irradiated or nonviable lyophilized pluripotent human stem cells may provide an in vivo "feeder" or "chaperone effect." Since this chaperone effect does not require differentiation or permanent integration or persistence of pluripotent stem cells, this technology may be viewed as a universal method to induce tissue repair, including but not limited to the heart, brain, spinal cord, lung, liver, and kidneys, without regard to MHC restrictions or need for immune suppression.

EXAMPLES

Example 1

Lyophilization of Embryonic Stem Cells

Lyophilization is a method of dehydration to preserve material so it does not decay and is easy to transport and store. The material is first pretreated to concentrate it in a freeze-drying protectant, such as trehalose. The material is then frozen to very low temperatures such as −80° C., and subsequently dehydrated by sublimation under low pressure vacuum.

No living cells remain after lyophilization. The lyophilized cells can be stored indefinitely at room temperature or colder temperatures and rehydrated, reconstituted, or otherwise suspended in media, matrix, or bandage as needed before use or used directly without rehydration in powder form.

Example 2

Wound Healing Using Lyophilized ESC Powder

ICR (imprinting control region) mice (8 weeks old; female; body weight, 20-23 g) were obtained from Harlan. The animals were randomly divided into four groups: 1) lyophilized nonviable murine embryonic stem cells ("ESC powder"), 2) lethally irradiated nonviable murine embryonic stem cells ("iESC"), 3) irradiated murine nonviable fibroblasts control ("fibroblast control"), and 4) murine ESC conditioned media control ("media control"). The excisional wound-splinting model was generated. There were eight animals in the media control group and nine animals in each of the remaining groups.

After hair removal from the dorsal surface and anesthesia, two 6-mm full-thickness excisional skin wounds were created on each side of the midline. The mice were then treated with one of the four treatments. Each mouse received the same treatment to both wounds.

Each wound treated with cells received approximately 1 million stem cells: $1.0 \times 10^6$ cells (lethally irradiated (100 Gy) nonviable ESC or lethally irradiated (100 Gy) nonviable fibroblasts) in 60 µl of PBS injected intradermally around the wound at four injection sites and $0.3 \times 10^6$ cells in 20 µl of growth factor-reduced Ma trigel (BD Biosciences) applied onto the wound bed. The lyophilized ESC powder containing approximately 1 million embryonic stem cells was resuspended in PBS and injected intradermally as described above. Conditioned media without cells was also used as a control. A donut-shaped silicone splint was placed so that the wound was centered within the splint. An immediate-bonding adhesive (Krazy Glue, Columbus, Ohio) was used to fix the splint to the skin, followed by interrupted sutures to stabilize its position, and Tegaderm (3M, London, ON, Canada) was placed over the wounds. The animals were housed individually.

Figure 2:
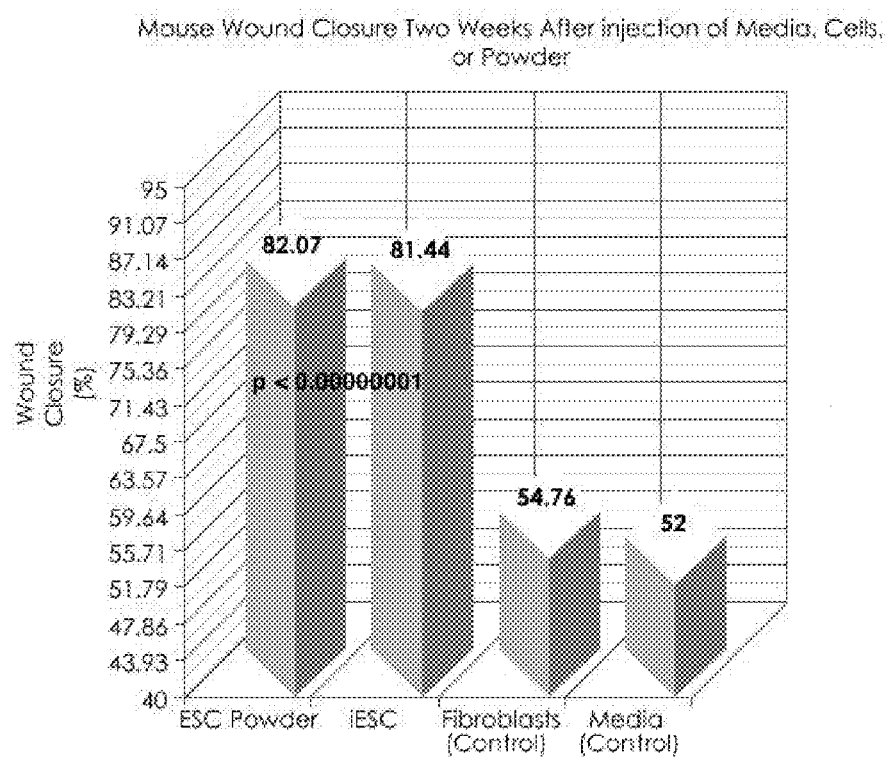
FIG. 2 is a bar graph showing that ESC powder and lethally irradiated embryonic stem cells increase the rate at which wounds close compared to fibroblast and media only controls.

Wound closure was analyzed two weeks after treatment. The wounds were photographed and the wound opening was digitally measured. The results are presented in FIGS. 1 and 2. FIG. 1 includes the percent wound closure for both wounds of each animal and FIG. 2 shows the mean percent wound closure for each group with statistically significant p value ($p<0.00000001$) when compared to either fibroblasts or media control. The wounds treated with lyophilized ESC powder or lethally irradiated ESC healed very similarly and nearly 30 percent better than the fibroblasts and media control groups. It was concluded that treatment with the nonviable stem cells, either in powder or lethally irradiated form, is effective to increase the rate at which the wounds close.

Example 3

Anti-Aging Cream Using Lyophilized Human ESC Powder

The use of face cream containing lyophilized human embryonic stem cells was evaluated for anti-aging benefits. The face cream was prepared from all natural components (stearic acid, emulsifying wax, oil, and water) to which the lyophilized human ESC powder was added. However, in another manner the lyophilized human ESC powder could be added ("mixed or stirred into") any commercially available cream, lotion, soap, or other cosmetic product. Lyophilized embryonic stem cell powder was mixed into the cream as a powder without hydration at a concentration of 1 million powder lyophilized cells per ounce of cream, although concentration of powder added to cream or lotion or other cosmetic base can be adjusted based on product price range and desired effect.

The performance of the cream was evaluated over an eight week period with five healthy, Caucasian female test subjects between the ages of 35 to 55. The test subjects abstained from using any self-tanning, anti-aging, and moisturizing products, including lotions, creams, gels, and nutritional supplements for at least 72 hours prior to the commencement of the study and used only the experimental face cream during the test period. The test subjects had fine lines and wrinkles on their faces such that any differences due to effectiveness of the cream could be measured.

Baseline measurements were taken for each test subject prior to the first use of the cream. Measurements were taken thereafter at 28 and 56 days of use. The test subjects were instructed to apply the cream topically to the face twice daily. They were also instructed to use a loofah and not apply the cream to mucosal surfaces (i.e., lips, mouth, eyes) and to not apply additional makeup on top of the cream.

At the described times, surface evaluation of the skin was analyzed by Visioscan (Courage and Khazaka), which takes a direct image of the living skin using a measuring head containing a CCD-camera and two metal halogen lamps positioned opposite each other in order to ensure even illumination of the measuring field on the skin. The grey level distribution of the pixels in the image correspond to different phenomena (white pixels represent desquamation on the skin, dark pixels represent lines and wrinkles). The software with the Visioscan automatically calculates skin smoothness, skin roughness, scaliness and wrinkle parameters. (Fischer, T. W., et al., Direct and non-direct measurement techniques for analysis of skin surface topography, Skin Pharmacol Appl Skin Physiol 1999; 12:1-11; Grether-Beck, S., et al., An EC-derived Tetrapeptide to Counterbalance ECM Degeneration, Cosmetic & Toiletries magazine, Vol. 124 Np. 6/June 2009, both of which are incorporated herein by reference.)

A Nova Dermal Phase Meter, Model DPM 9003 (NOVA Technology Corp., Gloucester, Mass.) was used to obtain measurements of skin surface impedance to determine electroconductivity of the treatment sites. This meter provides a relative measure of the retained water content of the skin as a function of the skin's dielectric value. Skin impedance was recorded automatically when equilibrium was achieved. (Leveque, J. L., et al., Impedance Methods for Studying Skin Moisturization, J. Soc. Cosmet. Chem., 34: 419-428, 1983, which is incorporated herein by reference.)

Detailed, high resolution before and after digital photographs were taken with fixed camera background, angles, settings, lighting, test subject positioning, color bars, white balance, standardized, and digitally certified unretouched. Photographs were evaluated using the Visioscan image analysis software which allows the evaluation parameter to be captured and quantified. The image analysis software detected subtle changes in color by three dimensional profile of hue, value, and chroma. These characteristics were translated into color coordinates (a*, b* and L*) whose spacing is considered with the color changes perceived by the human eye. This software also allowed wrinkles to be captured and quantified. The size of the area of involvement differed for each test subject; therefore, percent difference was calculated individually and then averaged.

None of the subjects had adverse or unexpected reactions of any kind during treatment.

Figure 3:
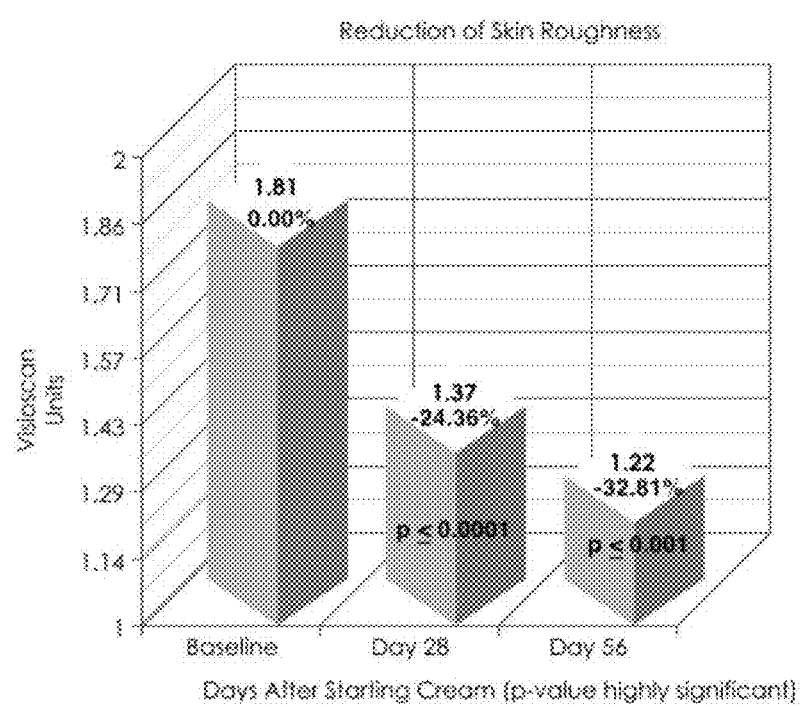
FIG. 3 is a bar graph demonstrating the reduction in skin roughness after treatment of humans with cream containing human lyophilized ESC powder.

As shown in Table 1 below and in FIG. 3, treatment with the cream resulted in dramatic decreases in the Visioscan parameters of surface roughness (SEr) associated with the depth of fine and coarse wrinkles. The reductions were statistically significant after 28 and 56 days of use.

TABLE 1

Surface Evaluation of Living Skin Via Visioscan - Reduction of Fine and Coarse Wrinkles (SEr)

| Subject | Baseline | Day 28 | Individual % Difference Day 28 | Day 56 | Individual % Difference Day 56 |
|---|---|---|---|---|---|
| 1 | 1.98 | 1.47 | −25.76% | 1.35 | −31.99% |
| 2 | 1.40 | 0.95 | −32.14% | 0.87 | −37.86% |
| 3 | 2.29 | 1.84 | −19.65% | 1.72 | −24.89% |
| 4 | 1.55 | 1.21 | −22.10% | 1.13 | −27.25% |
| 5 | 1.82 | 1.37 | −24.73% | 1.01 | −44.51% |
| Mean | 1.81 | 1.37 | | 1.22 | |
| % Difference | | | −24.36%* | | −32.81%* |
| p | | | 0.000* | | 0.001* |
| t | | | 6.767* | | 4.985* |
| Max % Improvement | | | 32.14% | | 44.51% |

*Statistically significant

Figure 4:
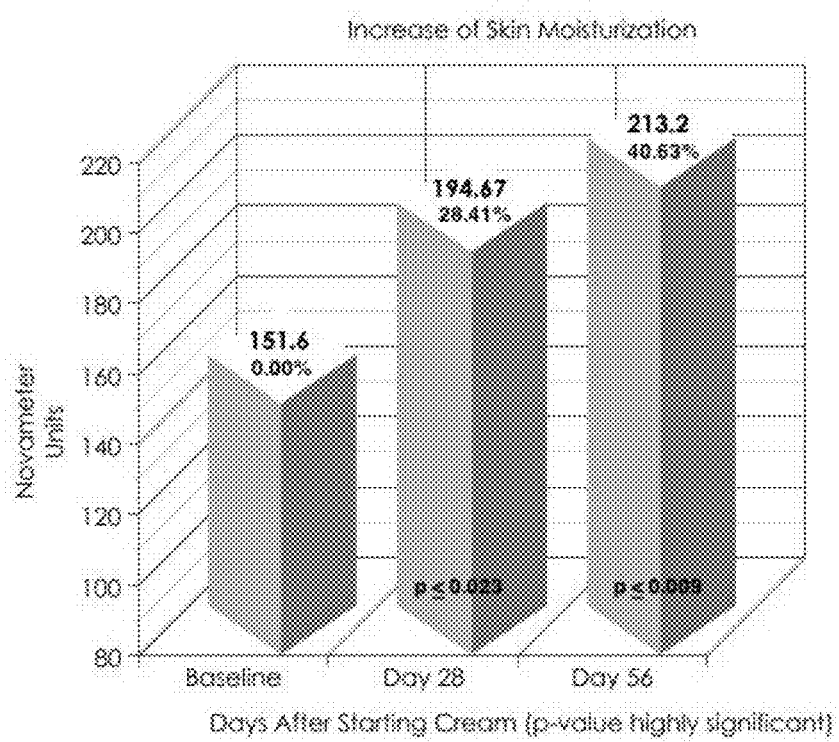
FIG. 4 is a bar graph showing that treatment with cream containing human lyophilized ESC powder increases skin moisturization in humans.

As shown in Table 2 below and in FIG. 4, the Novameter readings demonstrated that the cream dramatically increased the skin moisture content. The increases were statistically significant after 28 and 56 days of use.

TABLE 2

Electroconductivity Via Novameter - Skin Moisturization Evaluation

| Subject | Baseline | Day 28 | Individual % Difference Day 28 | Day 56 | Individual % Difference Day 56 |
|---|---|---|---|---|---|
| 1 | 123.33 | 170.00 | 37.84% | 190.00 | 54.06% |
| 2 | 158.67 | 197.33 | 24.37% | 248.67 | 56.72% |
| 3 | 200.00 | 286.00 | 43.00% | 288.67 | 44.34% |
| 4 | 145.33 | 175.33 | 20.64% | 182.00 | 25.23% |
| 5 | 130.67 | 144.67 | 10.71% | 156.67 | 19.90% |
| Mean | 151.60 | 194.67 | | 213.20 | |
| % Difference | | | 28.41%* | | 40.63%* |
| p | | | 0.023* | | 0.009* |
| t | | | 2.732* | | 3.289* |
| Max % Improvement | | | 43.00% | | 56.72% |

*Statistically significant

Figure 5:
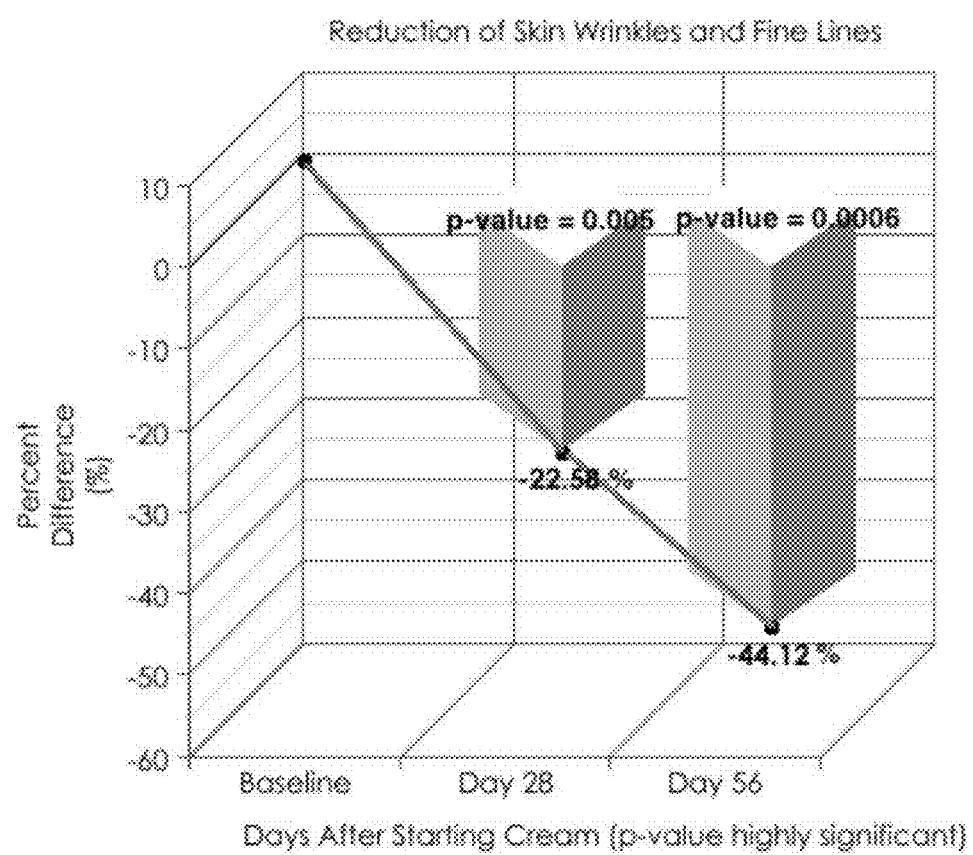
FIG. 5 is a bar graph showing that treatment with cream containing human lyophilized ESC powder decreases skin wrinkles and fine lines in humans.

As shown in Table 3 below and FIG. 5, data obtained through the image analysis software demonstrated wrinkle reduction after 28 and 56 days of usage of the cream. The results were statistically significant.

TABLE 3

Reverse Photo Engineering - Wrinkle and Fine Lines Reduction Analysis

| Subject | Baseline | Day 28 | Individual % Difference Day 28 | Day 56 | Individual % Difference Day 56 |
|---|---|---|---|---|---|
| 1 | 14936 | 12779 | −14.44% | 8210 | −45.03% |
| 2 | 53404 | 43101 | −19.29% | 34842 | −34.76% |
| 3 | 20991 | 12098 | −42.37% | 8181 | −61.03% |
| 4 | 25869 | 20736 | −19.84% | 17957 | −30.58% |
| 5 | 24916 | 20692 | −16.95% | 12659 | −49.19% |
| % Difference | | | −22.58%* | | −44.12%* |
| P | | | | | 0.005* |
| T | | | | | 3.676* |
| Max % Reduction | | | −42.37% | | −61.03% |

*Statistically significant

Figure 6:
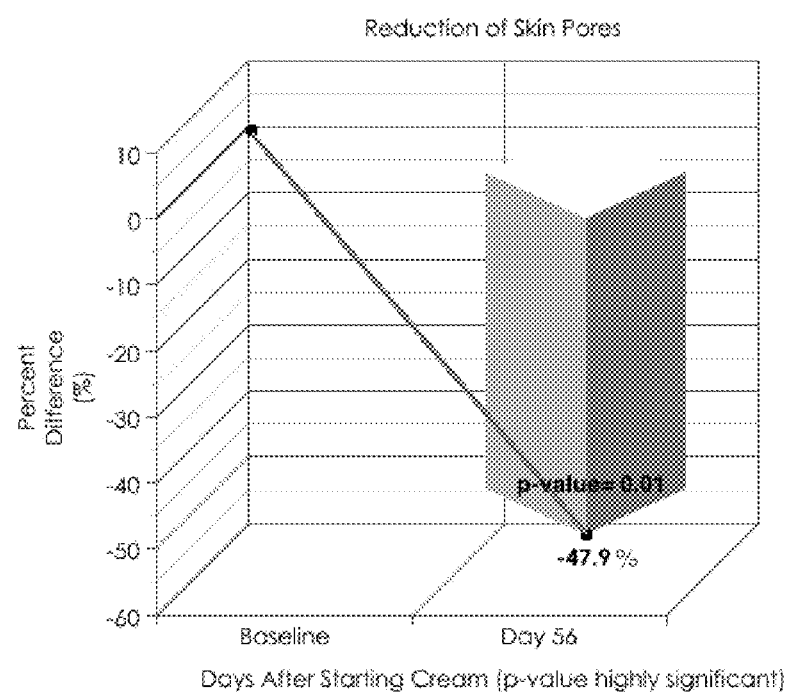
FIG. 6 is a bar graph showing that treatment with cream containing human lyophilized ESC powder decreases pore size in humans.

As shown in FIG. 6, skin pore size was also measured over the course of the 56 day treatment. Detailed, high resolution before and after digital photographs were taken, with fixed camera background, distances, angles, settings, lighting, panelist positioning, color bars, white balance, standardized and digitally certified unretouched. Each stage in the progression of the treatment was photographically documented and the test area of involvement isolated. Photographs were evaluated using image analysis software which allows the visible pores to be captured and quantified. As shown in FIG. 6, the mean size of the pores was reduced from baseline by 47.9% at day 56 (p-value=0.01).

The test subjects also completed questionnaires regarding the cream as presented in Table 4 below. The results from the questionnaire corroborated the instrumental data.

TABLE 4

Questionnaire Results

| Questions | Time Point | Agree | Disagree |
|---|---|---|---|
| 1) Skin appears dramatically more hydrated | Day 28 | 60.00% | 40.00% |
| | Day 56 | 80.00% | 20.00% |

TABLE 4-continued

Questionnaire Results

| Questions | Time Point | Agree | Disagree |
|---|---|---|---|
| 2) Skin feels significantly more hydrated | Day 28 | 80.00% | 20.00% |
|  | Day 56 | 80.00% | 20.00% |
| 3) Test products significantly improve skin's softness and smoothness | Day 28 | 80.00% | 20.00% |
|  | Day 56 | 80.00% | 20.00% |
| 4) Test products significantly reduce roughness and dryness | Day 28 | 80.00% | 20.00% |
|  | Day 56 | 80.00% | 20.00% |
| 5) Test products significantly improve skin's radiance | Day 28 | 80.00% | 20.00% |
|  | Day 56 | 80.00% | 20.00% |
| 6) Test products significantly improve skin's dullness | Day 28 | 80.00% | 20.00% |
|  | Day 56 | 80.00% | 20.00% |
| 7) Test products significantly improve skin clarity, leaving a healthy, even tone | Day 28 | 60.00% | 40.00% |
|  | Day 56 | 60.00% | 40.00% |
| 8) Face appears significantly brighter | Day 28 | 60.00% | 40.00% |
|  | Day 56 | 80.00% | 20.00% |
| 9) Test products significantly reduce skin's discoloration | Day 28 | 60.00% | 40.00% |
|  | Day 56 | 60.00% | 40.00% |
| 10) Face appears significantly more youthful | Day 28 | 80.00% | 20.00% |
|  | Day 56 | 60.00% | 40.00% |
| 11) Skin looks significantly more luminous | Day 28 | 80.00% | 20.00% |
|  | Day 56 | 60.00% | 40.00% |
| 12) Skin feels significantly firmer | Day 28 | 60.00% | 40.00% |
|  | Day 56 | 60.00% | 40.00% |
| 13) Skin looks significantly tighter | Day 28 | 80.00% | 20.00% |
|  | Day 56 | 60.00% | 40.00% |
| 14) Test products dramatically reduce the appearance of fine lines and wrinkles | Day 28 | 60.00% | 40.00% |
|  | Day 56 | 60.00% | 40.00% |
| 15) Test products dramatically reduce the appearance of crow's feet around the eyes | Day 28 | 60.00% | 40.00% |
|  | Day 56 | 60.00% | 40.00% |
| 16) Lines and wrinkles appear dramatically smoother and softer | Day 28 | 80.00% | 20.00% |
|  | Day 56 | 60.00% | 40.00% |
| 17) Test products significantly improve skin's overall appearance | Day 28 | 80.00% | 20.00% |
|  | Day 56 | 80.00% | 20.00% |
| 18) Test products significantly improve skin's overall health | Day 28 | 60.00% | 40.00% |
|  | Day 56 | 80.00% | 20.00% |

Example 4

Acute Myocardial Infarction Treated with Injection of Lyophilized ESC Powder

Mice underwent intraperitoneal anesthesia with a mixture of ketamine (100 mg/kg), xylazine (10 mg/kg), and atropine (0.04 mg/kg), and were ventilated via a rodent ventilator (Harvard model 687 mouse ventilator; Harvard Apparatus, Holliston, Mass.). Left thoracotomy was performed at the fourth intercostal space. The chest wall was retracted by the use of 5-0 silk or monofilament suture. Ligation proceeded with a 7-0 silk suture passed with a tapered needle underneath the left anterior descending branch of the left coronary artery <2 mm from the tip of normally positioned left auricle. A 1-mm section of PE-10 tubing was placed on the top of the vessel, and a knot was tied on the top of the tubing to occlude the coronary artery. The knot was cut after occlusion for 60 minutes to restore reperfusion.

The mice were divided into three groups: 1) lyophilized murine ESC powder prepared according to Example 1 and resuspended in PBS; 2) lethally irradiated murine ESC; and 3) conditioned media control. Six animals were in each group.

Figure 7:
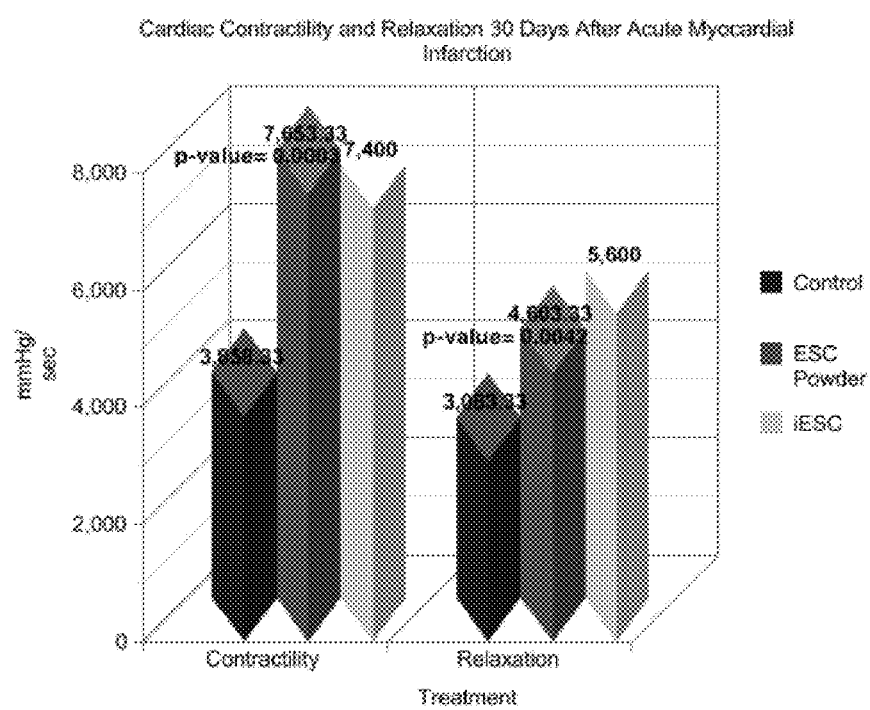
FIG. 7 is a bar graph demonstrating that treatment with lyophilized ESC powder as well as lethally irradiated ESC improves mouse cardiac contractility and relaxation compared to control 30 days after acute myocardial infarction. Injection of media alone (negative control) did not improve heart function.

Three intramyocardial injections of 10 µL was performed in each animal using (depending upon group) either conditioned media, or $\approx 1\times 10^6$ lethally irradiated ESCs in PBS, or lyophilized powder from $\pm \approx 1\times 10^6$ ESCs rehydrated in PBS. Injections were performed into the infarction, border, and normal zones via a microsyringe. After chest wall closure, the mouse was removed from the respirator, endotracheal tube was withdrawn, warmth was maintained by a heating pad, and 100% oxygen via nasal cone was provided under intensive care until full recovery. Cardiac contractility and relaxation were monitored via a high-fidelity transducer-tipped pressure catheter (SPR 839; Millar Instruments, Houston, Tex.). Signals were digitized by use of a data translation series analog digital converter and then stored and analyzed on a Millar PVAN data acquisition and analysis system. Values derived from pressure traces were averaged over no less than 20 beats. The cardiac contractility and relaxation data 30 days after treatment are shown as mean values of all animals in each group with P values in FIG. 7 and Table 5 below. Importantly, lyophilized ESC powder significantly improved heart function compared to media treated hearts and lyophilized ESC powder was as effective and not statistically different from injection of lethally irradiated ESC in heart function. Lethally irradiated ESC were used as a positive control because application has previously demonstrated that mitotically inactivated ESC are capable of inducing endogenous murine cardiac tissue regeneration. (Burt et al: *"Mitotically inactivated embryonic stem cells can be used as an in vivo feeder layer to nurse damaged myocardium after acute myocardial infarction: a preclinical study,"* Circulation Research, 2012, Oct. 26; 111(10):1286-96), which is incorporated herein by reference.

TABLE 5

Cardiac Contractility and Relaxation 30 Days After Acute Myocardial Infarction

|  | Control | ESC Powder | iESC |
|---|---|---|---|
| Contractility (mmHg/sec) | 3858.33 | 7653.33 (p-value = 0.0003) | 7400 |
| Relaxation (mmHg/sec) | 3083.33 | 4603.33 (p-value = 0.0042) | 5600 |

Example 5

Cardiac Ischemia in Rhesus Macaque Monkeys Treated with Lethally Irradiated ESC

Three to four year old Rhesus macaque monkeys underwent open thoractomy under general anesthesia. After dissection and visualization, the left anterior descending (LAD) coronary artery was ligated for approximately 45 minutes. Myocardium distal to the infarct became pale, visibly ischemic, and non-contractile.

After 45 minutes, four monkeys were treated with $5\times 10^6$ lethally irradiated nonviable human ESC and four monkeys were controls treated with conditioned media from the supernatant of human ESC by injection into the ischemic penumbra. The coronary artery ligation was removed and the sternotomy closed. Cardiac function was evaluated by a high fidelity transducer tipped catheter (Millar Instruments, Houston, Tex.) readings and magnetic resonance imaging (MRI) of left ventricular function performed 30 to 45 days after infarction.

Figure 8:
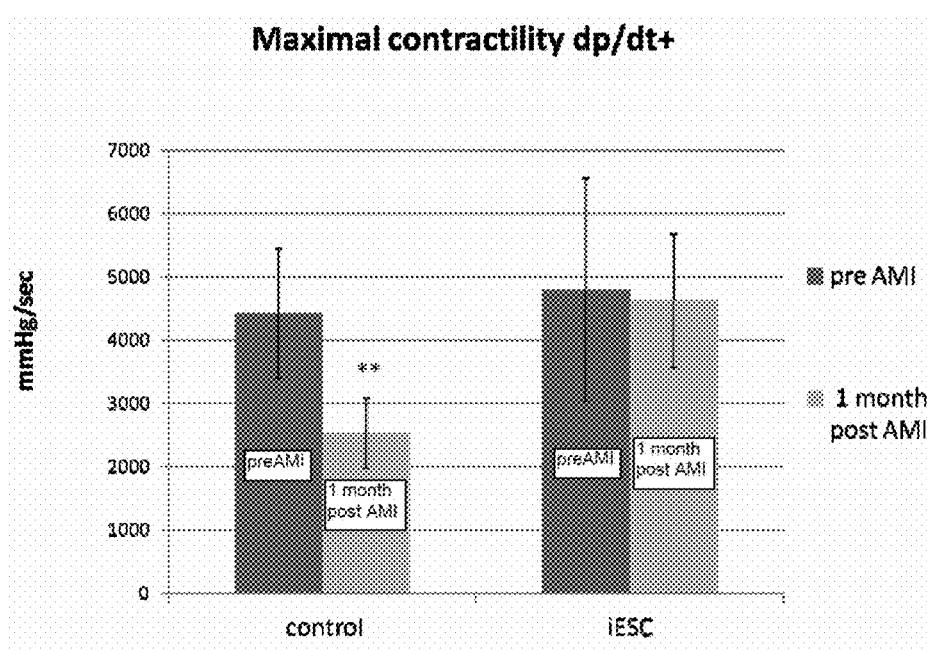
FIG. 8 is a bar graph showing Rhesus Macaque monkey cardiac contractility (dp/dt+) in normal hearts and 30 days after acute myocardial infarction and injection of either conditioned media (control) or lethally irradiated (100 Gy, single fraction) human ESC.

All monkeys treated with lethally irradiated ESC had rapid recovery and/or returned to normal heart function. FIG. 8 demonstrates that 30 days after acute myocardial infarction monkeys treated with conditioned media had a large decline in systolic contractility compared to preinfarction (maximal mean systolic contraction 4400 mmHg/sec in iESC treated mice compared to 2300 mmHg/sec in controls). In comparison, monkeys treated with lethally irradiated human embryonic stem cells (iESC) had preservation of myocardial function one month later (mean 4600 mmHg/sec to 4500 mmHg/sec) ($P<0.05$).

Figure 9:
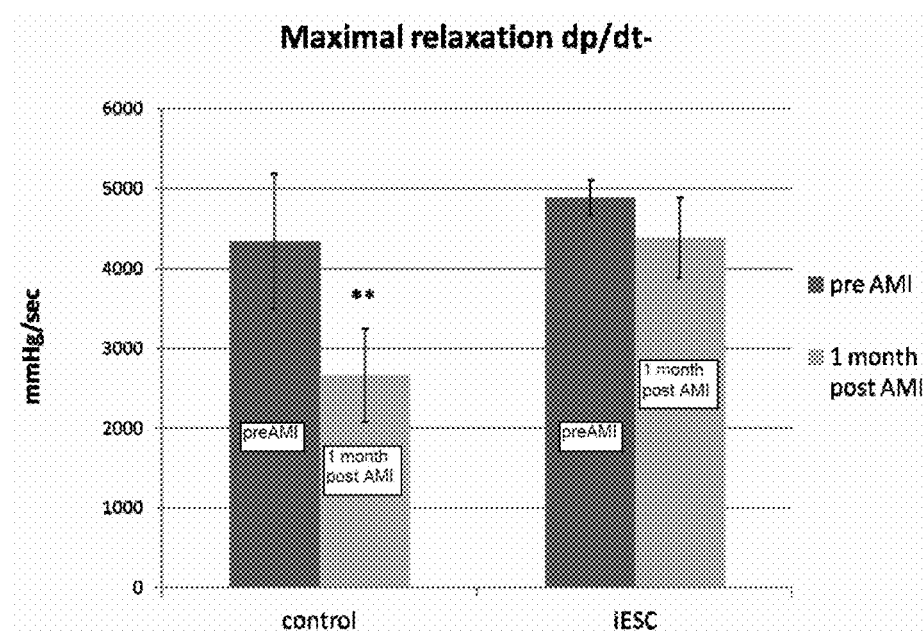
FIG. 9 is a bar graph showing Rhesus Macaque monkey cardiac relaxation (dp/dt−) in normal hearts and 30 days after acute myocardial infarction and injection of either conditioned media (control) or lethally irradiated (100 Gy, single fraction) human ESC.

As shown in FIG. 9, the diastolic function of the heart was also preserved after an acute heart attack when treated with lethally irradiated human ESC compared to media treated controls. In the controls, maximal mean relaxation decreased from 4300 mmHg/sec to 2600 mmHg/sec. In acute ischemic hearts treated with lethally irradiated human ESC maximal mean diastolic relaxation was similar before infarction and 30 days after infarction (mean maximal relaxation 4800 mmHg/sec versus 4600 mmHg/sec) (FIG. 9) ($P<0.05$).

Figure 10:
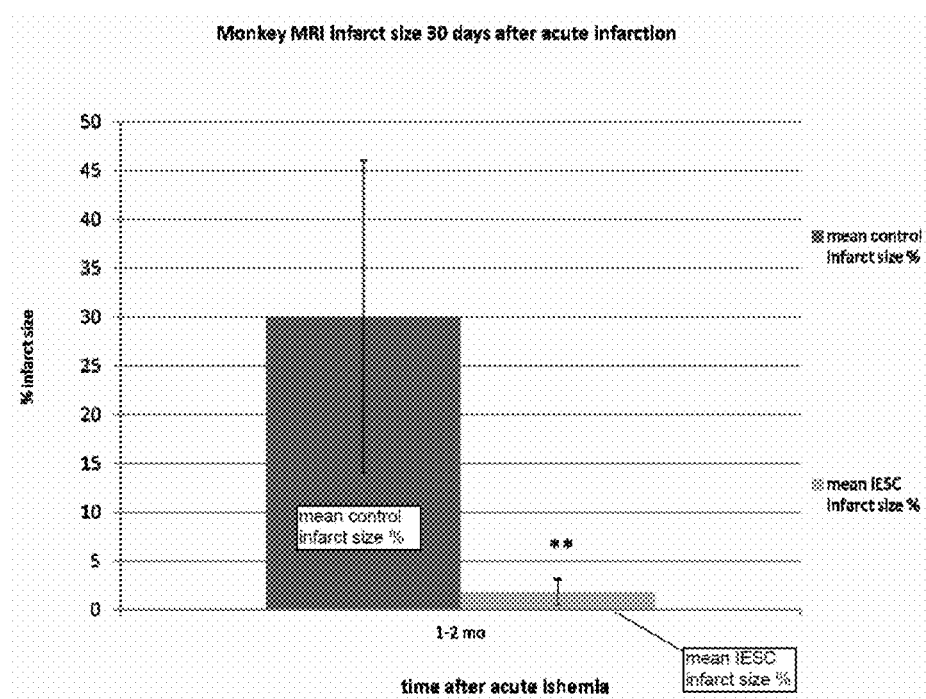
FIG. 10 is a bar graph showing Rhesus Macaque monkey infarct size by magnetic resonance imaging (MRI) 30 days after acute myocardial infarction and injection of either conditioned media (control) or lethally irradiated (100 Gy, single fraction) human ESC.
Figure 11:
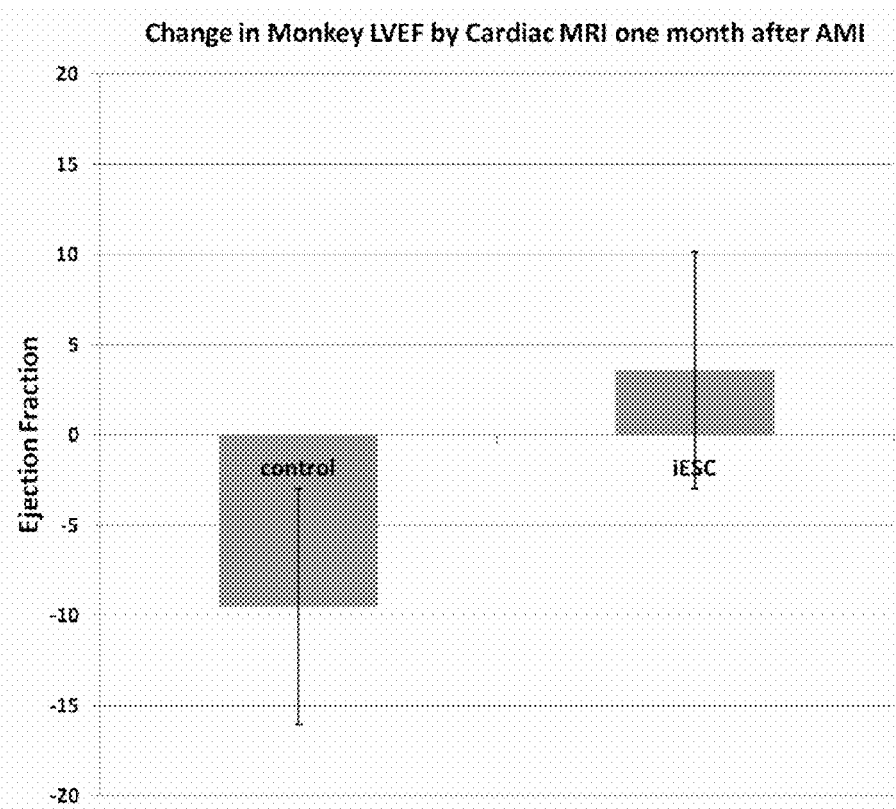
FIG. 11 is a bar graph showing change in cardiac ejection fraction 1 month after acute ischemia in monkeys treated with lethally irradiated human ESC versus controls treated with conditioned media.

Finally, magnetic resonance imaging (MRI) was used to determine infarct size 30 days after acute myocardial infarction in primates treated with lethally irradiated human ESC compared to those receiving only media after acute infarction (controls). FIG. 10 demonstrates virtually no tissue infarct 30 days after acute ischemia in monkeys treated with lethally irradiated human ESC versus mean 22 percent infarct size in media controls. FIG. 11 demonstrates decreased left ventricle ejection fraction 30 days after myocardial infarction compared to no decrease in injection fraction in monkeys treated with lethally irradiated human ESC. MRI also demonstrated no abnormal growths or pathology in the heart 8-10 months after injection of iESC.

Example 6

Irradiated ESC Fail to Proliferate or Survive Either Ex Vivo or In Vivo

Figure 12:
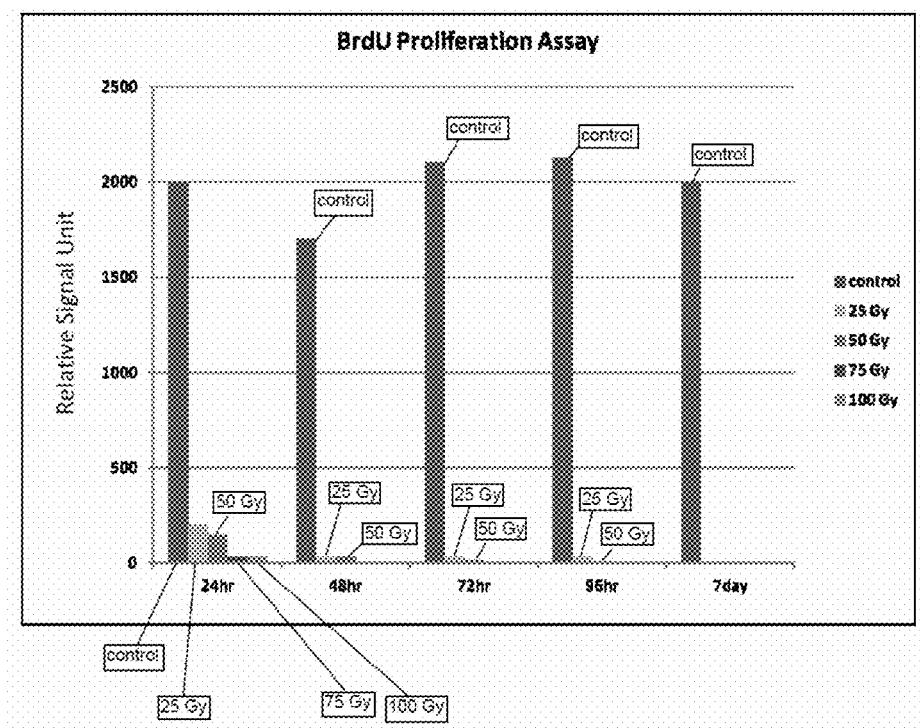
FIG. 12 is a bar graph showing the proliferation ability of mouse ESC treated with different doses of radiation and different durations of treatment.
Figure 13:
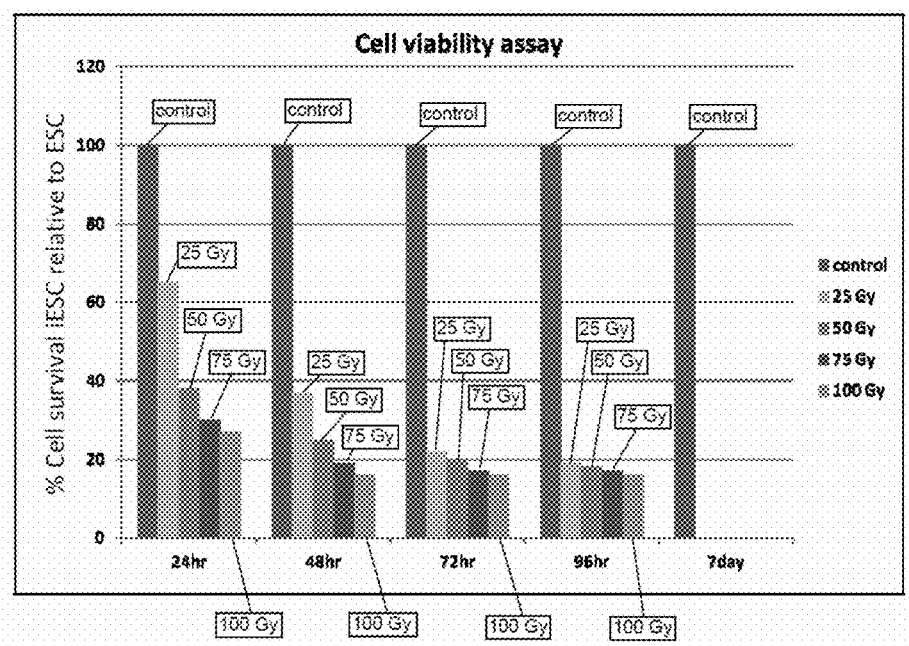
FIG. 13 is a bar graph showing cell viability of mouse ESC following treatment with different doses of radiation.

Irradiation inhibited ESC proliferation and prevented ESC viability. When exposed to irradiation in culture, ESC proliferation was not detectable after 72 hours at doses ≥50 Gy (FIG. 12), and viability was extinguished by seven days post irradiation (FIG. 13).

Example 7 iESC Exist Transiently In Vivo

Figure 14:
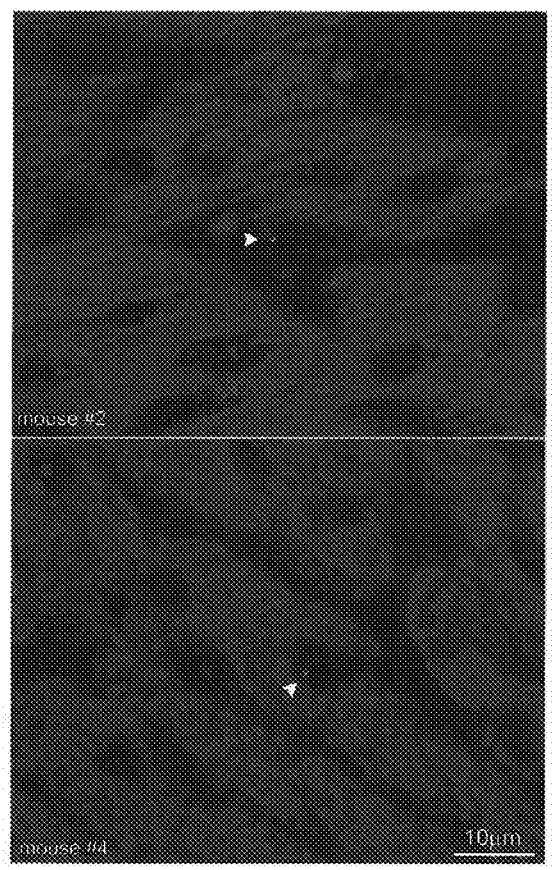
FIG. 14 is a photograph of fluorescent in situ hybridization of myocyte nuclei positive for ESC Y-chromosome DNA one month after ischemia-induced myocardial infarct in female mice and intra-myocardial injection of male lethally irradiated ESCs.

To determine if injected lethally irradiated ESC survived within the myocardium of recipient mice, male (Y chromosome positive) lethally irradiated ESC (100 Gy) were injected into the peri-infarct myocardium of female mice. One month after coronary artery ligation, hearts were studied for the remaining Y-chromosome by fluorescent in situ hybridization (FISH). The Y chromosome was detectable in less than 0.000025% (1 in 40,000) cardiac cells (FIG. 14), a level of stem cell DNA persistence previously attributable in the literature to the clinically insignificant and rare occurrence of cell fusion between donor stem cells and cardiomyocytes GM Nygren et al., Bone marrow-derived hematopoietic cells generate cardiomyocytes at a low frequency through cell fusion, but not transdifferentiation, *Nat Med.*, 10(5): 494-501 (2004)).

Example 8

In Vivo Cardiomyocyte DNA Synthesis is Increased in Lethally Irradiated ESC Treated Hearts To determine if lethally irradiated ESC promoted cardiomyocyte DNA synthesis in vivo, cell treated infarcted mice were injected beginning on the day of myocardial infarction once a day for 5 consecutive days with 5-bromo-2'-deoyuridine (BrdU). BrdU is a synthetic nucleoside analog of thymidine that incorporates into DNA (but not RNA) during DNA synthesis.

One hour after the surgery, mice were administered with BrdU i.p. injection daily (75 mg/kg; Sigma) for 5 days. Mice hearts were harvested one month after surgery and fixed in 4% formaldehyde. The heart sections were embedded and cut into 5-um thick sections The BrdU antibody (Roche) was used to target the BrdU-positive cells in the infarcted heart, according to the manufacturer's protocol. Myocytes were identified by sarcomeric actin labeling. The percentage of BrdU positive myocyte nuclei was determined by confocal fluorescent microscopy.

Figure 15:
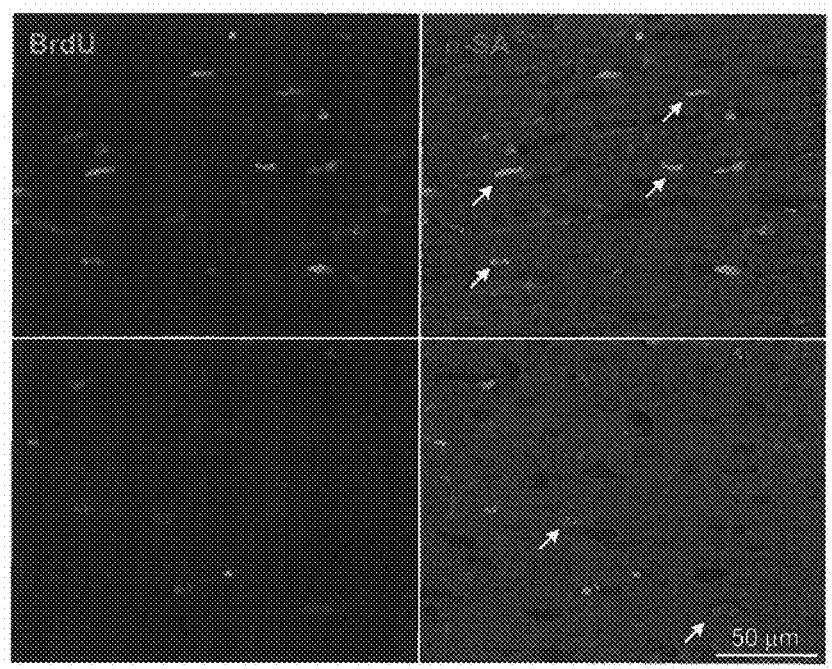
FIG. 15 is an image of immunofluorescent staining for 5-bromo-2-deoxyuridine (in green) one month after ischemia-induced myocardial infarct in female mice, with (top row) or without (bottom row) intra-myocardial injection of male irradiated embryonic stem cells.

One month later, mice were sacrificed and myocardium analyzed for BrdU. Streaks of BrdU positive cardiomyocytes were identified within the injured left ventricle; an average of 12 percent of cardiomyocytes were labeled by the halogenated nucleotide in the region bordering the infarct (FIG. 15). The corresponding value in the remote myocardium was 1.7 percent. In control untreated infarcted mice, BrdU labeled myocytes were 2 percent and 0.5 percent in the area adjacent to and distant from the scarred myocardium, respectively. Peri-infarct recipient cardiomyocyte DNA synthesis for iESC treated mice (12 percent) was significantly greater than the rare occurrence of y-chromosome iESC DNA (0.000025 percent).

Gene Expression Profile of Lethally Irradiated ESC Treated Hearts: Up-regulation of Proliferation, Chromosome Remodeling, and Metabolic Pathways; Down Regulation of Inflammatory Pathways Total RNA was isolated from murine heart tissues by using RNeasy Mini kit (Qiagen Corp., Venlo, Netherlands). Mouse hearts were placed in liquid nitrogen and grind with a motor and pestle. Tissue powder and liquid nitrogen was decanted into an Rnase-free, liquid-nitrogen-cooled, 2 ml micocentrifuge tubes with Buffer RLT (Qiagen Corp.). The lysate was pipeted directly into a QlAshredder spin column (Qiagen Corp.) placed in a 2 ml collection tube, centrifuge for 2 min at full speed, and supernatant was removed by pipetting, and transferred to a new microcentrifuge tube. One volume of 70% ethanol was added, mixed immediately by pipetting, and 700 ul of sample transferred to an RNeasy spin column placed in a 2 ml collection tube and centrifuge for 15 s at 8,000×g. Buffer RW1 (Qiagen Corp.) (700 ul) was added to the RNeasy spin column and centrifuge for 15 s at 8,000×g to wash the spin column membrane. The spin column membrane was washed twice by adding 500 Buffer RPE (Qiagen Corp.) to the RNeasy spin column and centrifuge for 15 s at 10,000×g. The RNeasy spin column was placed in a new 1.5 ml collection tube, 30-50 ul RNase-free water was added directly to the spin column membrane and centrifuge for 1 min at 8,000×g to elute the RNA.

Biotin labeled cRNA was generated from high quality total RNA using the Illumina TotalPrep RNA Amplification kit (Ambion). Briefly, 150 ng of total RNA with 260/280 absorbance ratio was reverse transcribed with an oligo (dT) primer bearing T7 promoter. The first strand cDNA, produced in the reaction, was used to make the second strand cDNA. Purified second strand cDNA along with biotin UTPs were used to generate biotinylated, antisense RNA of each mRNA in an in vitro transcription (IVT) reaction. Size distribution profile for the labeled cRNA samples were evaluated by a bioanalyzer. 750 ng of purified labeled cRNAs were hybridized at 55° C. over night with the MouseRef-8 v2 Expression BeadChip and washed the following day. Signals was developed with Streptavidin-Cy3 and scanned with an Illumina iScan System.

Microarray Data Analysis

RNA expression analysis was performed using the Illumina MouseRef-8 BeadChip, which provides coverage of around 25,700 genes and expressed sequence tags. Heart tissue cells were treated with either media or embryonic stem cells (ESC) and their RNA was collected at various time points at 12 hours, 24 hours, 3 days, 7 days, and 28 days. Raw signal intensities of each probe were obtained using data analysis software (Beadstudio; Illumina) and imported to the Lumi package of Bioconductor for data analysis before transformation and normalization (see P. Du et al., Bioinforma tics, 24(13): 1547-8 (2008); S. Lin et al., Nucleic Acids Res., 36(2): ell (2008); P. Du et al., Biol. Direct. 2: 16 (2007)). A/P call detection was performed based on detection p value. 13,873 out of 25,697 probes with less than 0.01 were considered as valid signals. Then the maximum signal difference for each probe was calculated and 8167 probes were kept by 2-fold cutoff. These preselected probes were imported into time course package, EDGE (J. Leek et al., Bioinformatics, 22, 507-508 (2006)), to perform a standard analysis of time dependent treatment effects. With the threshold of 0.1 q value, 539 unique genes were identified as significant genes involved in ESC treatment. For each time point, differentially expressed genes were identified using an Analysis of Variance (ANOVA) model with empirical Bayesian variance estimation (J. M. Wettenhall et al., Bioinformatics 20: 3705-3706 (2004)). Initially, genes were identified as being differentially expressed on the basis of a statistically significant (raw p-value <0.01), and 2-fold change (up or down) in expression level in ESC-treated RNA samples compared to controls.

Figure 16:
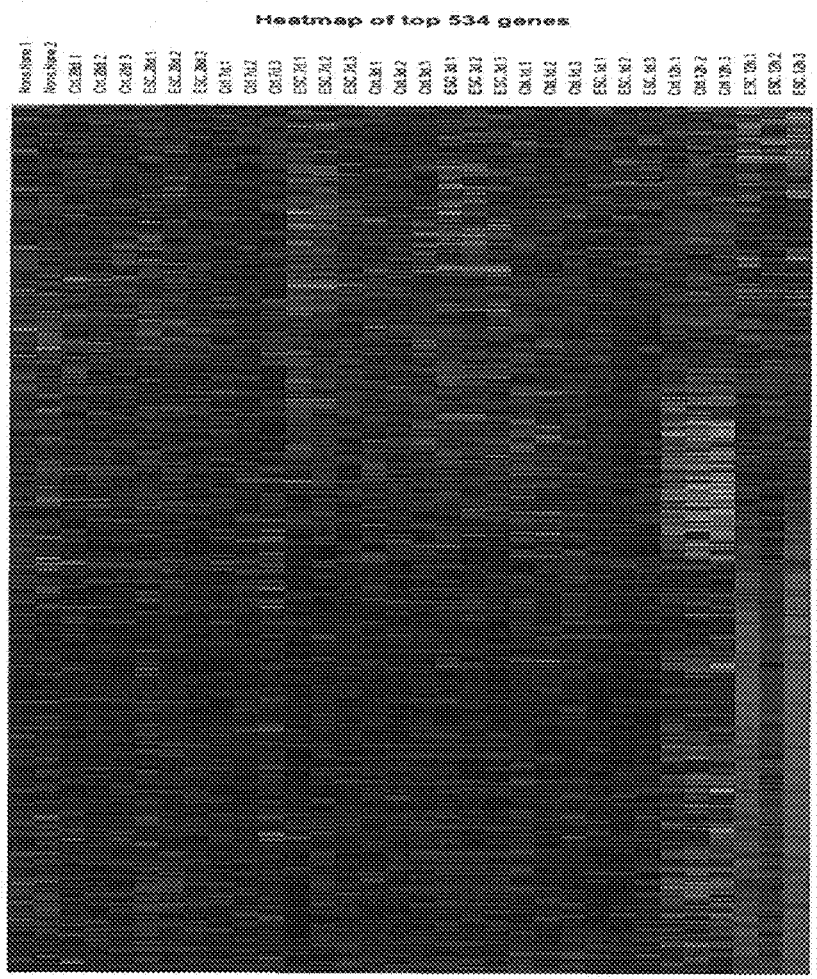
FIG. 16 is a heat map of 534 genes differentially expressed between lethally irradiated ESC treated and media treated hearts at different time points after acute myocardial infarction.

Gene expression profile from microarrays were performed to evaluate differences in gene expression between lethally irradiated ESC treated hearts and conditioned media treated hearts at 12 hours and 1, 3, 7, and 28 days after acute myocardial infarction (FIG. 16).

Between lethally irradiated ESC and media treated hearts, 539 genes were expressed differentially (>2 fold increase or decrease) at 12 hours, 39 genes at 24 hours, and 7 genes at 3 days after acute myocardial infarction. There was no difference in gene expression profile between conditioned media and iESC treated mice at 7 and 28 days after treatment. By 28 days after treatment, the gene expression profile of iESC treated mice was no different from normal hearts.

Differences between highly expressed genes (in red) and lower expression levels (in green) abated over time and were not different in expression profile from normal (non-infarcted) hearts by 28 days after myocardial infarction (FIG. 16). The 20 most up-regulated and down-regulated cell signal pathways in iESC treated hearts after acute myocardial infarction are listed below in Table 6.

TABLE 6

Most up and down regulated cell signal pathways

| GO (Gene ontogeny) IDs | GO Terms | P-value | Fold change |
|---|---|---|---|
| Top 20 most up-regulated cell signal pathways by iESC treatment of infarcted heart tissue | | | |
| GO:0044260 | Cellular macromolecular metabolic process | 2.78e−44 | 163 |
| GO:0006139 | Nucleobase, nucleoside, nucleotide and nucleic acid metabolic process | 7.62e−41 | 129 |
| GO:0006259 | DNA metabolic process | 1.9e−40 | 53 |
| GO:0044249 | Cellular biosynthetic process | 1.08e−39 | 132 |
| GO:0006260 | DNA replication | 6.38e−38 | 35 |
| GO:0022403 | Cell cycle phase | 1.46e−37 | 48 |
| GO:0000279 | M phase | 3.68e−35 | 44 |
| GO:0000278 | Mitotic cell cycle | 3.16e−32 | 40 |
| GO:0034645 | Cellular macromolecule biosynthetic process | 9.16e−32 | 108 |
| GO:0009059 | Macromolecule biosynthetic process | 3.29e−31 | 108 |
| GO:0007067 | Mitosis | 1.87e−25 | 31 |
| GO:0000280 | Nuclear division | 1.87e−25 | 31 |
| GO:0000087 | M phase of mitotic cell cycle | 2.52e−25 | 31 |
| GO:0048285 | Organelle fission | 3.39e−25 | 31 |
| GO:0006974 | Response to DNA damage stimulus | 1.24e−22 | 32 |
| GO:0010457 | Gene expression | 5.94e−22 | 97 |
| GO:0051276 | Chromosome organization | 1.4e−21 | 36 |
| GO:0060255 | Regulation of macromolecule metabolic process | 1.58e−19 | 80 |
| GO:0080090 | Regulation of primary metabolic process | 3.57e−19 | 79 |
| GO:0051171 | Regulation of nitrogen compound metabolic process | 6.22e−19 | 73 |
| Top 20 most down-regulated cell signal pathways by iESC treatment of infarcted heart tissue | | | |
| GO:0006952 | Defense response | 13.81e−10 | 11 |
| GO:0009615 | Response to virus | 1.31e−7 | 5 |
| GO:0006954 | Inflammatory response | 3.43e−6 | 6 |
| GO:0002694 | Regulation of leukocyte activation | 5.61e−6 | 5 |
| GO:0050865 | Regulation of cell activation | 5.99−6 | 5 |
| GO:0008228 | Opsonization | 8.55e−6 | 2 |
| GO:0032020 | ISG-15 protein conjugation | 1.71e−5 | 2 |
| GO:0009611 | Response to wounding | 3.33e−5 | 6 |
| GO:0006935 | Chemotaxis | 4.07e−5 | 4 |
| GO:0001932 | Regulation of protein amino acid protein phosphorylation | 4.67e−5 | 4 |
| GO:0042325 | Regulation of phosphorylation | 6.24e−5 | 5 |

TABLE 6-continued

Most up and down regulated cell signal pathways

| GO (Gene ontogeny) IDs | GO Terms | P-value | Fold change |
|---|---|---|---|
| GO:0019220 | Regulation of phosphate metabolic process | 7e−5 | 5 |
| GO:0051174 | Regulation of phosphorus metabolic process | 7e−5 | 5 |
| GO:0051249 | Regulation of lymphocyte activation | 9.43e−5 | 4 |
| GO:0050829 | Defense response to gram negative bacterium | .000102 | 2 |
| GO:0001934 | Positive regulation of protein amino acid phosphorylation | .000115 | 3 |
| GO:0031399 | Regulation of protein modification process | .000117 | 4 |
| GO:0010562 | Positive regulation of phosphorus metabolic process | .000128 | 3 |
| GO:0042327 | Positive regulation of phosphorylation | .000128 | 3 |
| GO:0045937 | Positive regulation of phosphate regulation process | .000128 | 3 |

Following acute myocardial ischemia and lethally irradiated ESC injection, microarray cardiac expression gene profiling demonstrated up-regulation of genes involved in cell cycle, chromosome remodeling, and metabolism pathways while inflammatory pathways were down-regulated.

While the disclosure has been particularly described with reference to particular processes and embodiments, it will be appreciated that various alterations, modifications, and adaptations may be made by those skilled in the art based on the present disclosure and are intended to be within the spirit and scope of the embodied method as expressed in the appended claims.

What is claimed is:

1. A wound healing composition comprising non-viable lyophilized pluripotent stem cells dispersed in a pharmaceutically acceptable carrier, and the non-viable lyophilized pluripotent stem cells included in a therapeutically effective amount in the form of intact cells and fragments and cellular contents of the pluripotent stem cells.

2. The wound healing composition according to claim 1, wherein the pluripotent stem cells are embryonic stem cells.

3. The wound healing composition according to claim 1, wherein the lyophilized pluripotent stem cells do not include conditioned media.

4. The wound healing composition according to claim 1, wherein the therapeutically effective amount comprises about $5\times10^4$ to about $1\times10^8$ lyophilized nonviable pluripotent stem cells or cell contents thereof.

5. A wound healing composition comprising non-viable lyophilized pluripotent stem cells in a pharmaceutically acceptable carrier, the non-viable lyophilized pluripotent stem cells included in a therapeutically effective amount in the form of non-viable intact cells.

6. The wound healing composition according to claim 5, wherein the pluripotent stem cells are embryonic stem cells.

7. The wound healing composition according to claim 5, wherein the lyophilized pluripotent stem cells do not include conditioned media.

8. The wound healing composition according to claim 5, wherein the therapeutically effective amount comprises about $5\times10^4$ to about $1\times10^8$ lyophilized nonviable pluripotent stem cells.

9. A wound healing composition comprising a bioadhesive and non-viable lyophilized pluripotent stem cells dispersed in a pharmaceutically acceptable carrier, and the non-viable lyophilized pluripotent stem cells included in a therapeutically effective amount in the form of non-viable intact cells.

10. The wound healing composition according to claim 9, wherein the pluripotent stem cells are embryonic stem cells.

11. The wound healing composition according to claim 9, wherein the lyophilized pluripotent stem cells do not include conditioned media.

12. The wound healing composition according to claim 9, wherein the therapeutically effective amount comprises about $5\times10^4$ to about $1\times10^8$ lyophilized nonviable pluripotent stem cells.

* * * * *